United States Patent
Velasquez et al.

(10) Patent No.: US 9,611,208 B2
(45) Date of Patent: *Apr. 4, 2017

(54) BIO-BASED ACRYLIC ACID AND ITS DERIVATIVES

(71) Applicant: The Procter & Gamble Company, Cincinnati, OH (US)

(72) Inventors: Juan Esteban Velasquez, Cincinnati, OH (US); Dimitris Ioannis Collias, Mason, OH (US); Jane Ellen Godlewski, Loveland, OH (US); Janette Villalobos Lingoes, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/515,704

(22) Filed: Oct. 16, 2014

(65) Prior Publication Data

US 2015/0105584 A1    Apr. 16, 2015

Related U.S. Application Data

(60) Provisional application No. 61/891,568, filed on Oct. 16, 2013.

(51) Int. Cl.
| | |
|---|---|
| *C07C 51/377* | (2006.01) |
| *B01J 27/18* | (2006.01) |
| *C07C 51/353* | (2006.01) |
| *B01J 37/00* | (2006.01) |
| *B01J 37/08* | (2006.01) |
| *B01J 35/02* | (2006.01) |
| *B01J 37/10* | (2006.01) |
| *B01J 37/04* | (2006.01) |

(52) U.S. Cl.
CPC ......... *C07C 51/377* (2013.01); *B01J 27/1806* (2013.01); *B01J 37/0036* (2013.01); *B01J 37/08* (2013.01); *C07C 51/353* (2013.01); *B01J 35/023* (2013.01); *B01J 37/04* (2013.01); *B01J 37/105* (2013.01)

(58) Field of Classification Search
CPC .................................................. C07C 51/355
See application file for complete search history.

(56) References Cited

U.S. PATENT DOCUMENTS

| | | | | |
|---|---|---|---|---|
| 2,859,240 | A * | 11/1958 | Holmen ............... | C07C 51/377 502/208 |
| 4,729,978 | A | 3/1988 | Sawicki | |
| 4,786,756 | A | 11/1988 | Paparizos et al. | |
| 8,884,050 | B2 * | 11/2014 | Godlewski ........... | B01J 27/1806 560/212 |
| 2013/0274512 | A1 * | 10/2013 | Villalobos ............ | B01J 27/1806 562/599 |
| 2013/0274516 | A1 * | 10/2013 | Velasquez ............ | B01J 27/1806 562/599 |
| 2013/0274517 | A1 * | 10/2013 | Godlewski ........... | C07C 51/377 562/599 |

FOREIGN PATENT DOCUMENTS

| | | | | |
|---|---|---|---|---|
| GB | 1 489 832 A | | 10/1977 | |
| GB | 1489832 A | * | 10/1977 | ............. B01J 27/18 |
| WO | WO 2013/155245 A2 | | 10/2013 | |
| WO | WO 2013/155270 A2 | | 10/2013 | |
| WO | WO 2013/155291 A1 | | 10/2013 | |
| WO | WO 2013/155292 A2 | | 10/2013 | |
| WO | WO 2013/155295 A1 | | 10/2013 | |
| WO | WO 2013/155296 A1 | | 10/2013 | |
| WO | WO 2013/155297 A2 | | 10/2013 | |
| WO | WO 2013/155298 A1 | | 10/2013 | |

OTHER PUBLICATIONS

International Search Report and Written Opinion for PCT/US2014/060792, dated Feb. 13, 2015.
Kirk-Othmer Encyclopedia of Chemical Technology, vol. 1, pp. 342-369 (5th Ed., John Wiley & Sons, Inc., 2004.
Hong et al., *Appl. Catal. A: General* 396:194-200 (2011).
Gunter et al., *J. Catalysis* 148:252-260 (1994).
Tam et al., *Ind. Eng. Chem. Res.* 38:3873-3877 (1999).

* cited by examiner

*Primary Examiner* — Yong Chu
(74) *Attorney, Agent, or Firm* — Brent M. Peebles

(57) ABSTRACT

Lactic acid, lactic acid derivatives, or mixtures thereof are dehydrated using a catalyst and process to produce bio-acrylic acid, acrylic acid derivatives, or mixtures thereof. A method to produce the catalyst is also provided.

14 Claims, No Drawings

BIO-BASED ACRYLIC ACID AND ITS DERIVATIVES

FIELD OF THE INVENTION

The present invention generally relates to a catalyst, method of making the catalyst, and process of producing bio-based acrylic acid, acrylic acid derivatives, or mixtures thereof from lactic acid, lactic acid derivatives, or mixtures thereof.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers (SAP), which are used in disposable absorbent articles, including diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 (5$^{th}$ Ed., John Wiley & Sons, Inc., 2004). Petroleum-based acrylic acid contributes to greenhouse emissions due to its high petroleum derived carbon content. Furthermore, petroleum is a non-renewable material, as it takes hundreds of thousands of years to form naturally and only a short time to consume. As petrochemical resources become increasingly scarce, more expensive, and subject to regulations for $CO_2$ emissions, there exists a growing need for bio-based acrylic acid, acrylic acid derivatives, or mixtures thereof that can serve as an alternative to petroleum-based acrylic acid, acrylic acid derivatives, or mixtures thereof.

Many attempts have been made over the last 80 years to make bio-based acrylic acid, acrylic acid derivatives, or mixtures thereof from non-petroleum sources, such as lactic acid (also known as 2-hydroxypropionic acid), lactic acid derivatives (e.g. alkyl 2-acetoxy-propionate and 2-acetoxy propionic acid), 3-hydroxypropionic acid, glycerin, carbon monoxide and ethylene oxide, carbon dioxide and ethylene, and crotonic acid. From these non-petroleum sources, only lactic acid is produced today in high yield from sugar (≥90% of theoretical yield, or equivalently, ≥0.9 g of lactic acid per g of sugar) and purity, and economics which could support producing acrylic acid at a cost competitive to petroleum-based acrylic acid. As such, lactic acid or lactate presents a real opportunity of serving as a feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts; phosphate salts; mixtures of sulfate and phosphate salts; bases; zeolites or modified zeolites; metal oxides or modified metal oxides; and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst. As an example, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as propionic acid, CO, and $CO_2$. Omission of the base treatment caused increased amounts of the side products. Another example is Hong et al., *Appl. Catal. A: General* 396:194-200 (2011), who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as Gunter et al., *J. Catalysis* 148:252-260 (1994); and Tam et al., *Ind. Eng. Chem. Res.* 38:3873-3877 (1999). The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CSCl, $Cs_2SO_4$, KOH, CsOH, and LiOH. In all cases, the above referenced catalysts were tested as individual components, not in mixtures. Finally, the group suggested that the yield to acrylic acid is improved and the yield to the side products is suppressed when the surface area of the silica support is low, reaction temperature is high, reaction pressure is low, and residence time of the reactants in the catalyst bed is short.

Finally, the Chinese patent application 200910054519.7 discloses the use of ZSM-5 molecular sieves modified with aqueous alkali (such as $NH_3$, NaOH, and $Na_2CO_3$) or a phosphoric acid salt (such as $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylic acid derivatives, or mixtures thereof from lactic acid or lactate by processes, such as those described in the literature noted above, has demonstrated: 1) yields of acrylic acid, acrylic acid derivatives, or mixtures thereof not exceeding 70% at short residence times; 2) low selectivities of acrylic acid, acrylic acid derivatives, or mixtures thereof, i.e., significant amounts of undesired side products, such as acetaldehyde, 2,3-pentanedione, propionic acid, CO, and $CO_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions, such as polymerization reactions. Aside from depositing on the catalysts, these side products, even when present in only small amounts, impose additional costs in processing acrylic acid (when present in the reaction product effluent)

in the manufacture of SAP, for example. These deficiencies of the prior art processes and catalysts render them commercially non-viable.

Accordingly, there is a need for catalysts, methods of making the catalysts, and processes for the dehydration of lactic acid, lactic acid derivatives, or mixtures thereof to acrylic acid, acrylic acid derivatives, or mixtures thereof, with high yield, selectivity, and efficiency (i.e., short residence time), and high longevity catalysts.

SUMMARY OF THE INVENTION

In one embodiment of the present invention, a catalyst is provided. The catalyst comprises: a) the phosphate anions described by formulae (Ic) and (IIc):

(Ic)

and

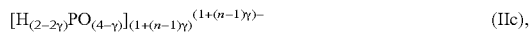

(IIc), and b) at least two different cations, wherein the catalyst is neutrally charged, wherein β and γ are greater or equal to 0 and less or equal to 1, wherein n is at least 2, wherein the molar ratio of said phosphate anions in said catalyst is between about 0.1 and about 10, wherein said at least two different cations comprise at least one monovalent cation and at least one polyvalent cation, and wherein said polyvalent cation is selected from the group consisting of the cations of the metals Be, Mg, Ca, Sr, Ba, Sc, Y, Ti, Zr, V, Nb, Cr, Mo, Mn, Ga, Si, Ge, B, Al, In, Tl, Sb, Sn, Bi, Pb, La, Ce, Er, Ac, Th, and mixtures thereof.

In another embodiment of the present invention, a method of preparing a catalyst is provided. The method comprises the following steps: a) combining $K_2HPO_4$, $Ba(NO_3)_2$, and $H_3PO_4$ to form a mixture, wherein the molar ratio of $Ba(NO_3)_2$, $K_2HPO_4$, and $H_3PO_4$ is about 3:1:4; b) calcining said mixture at about 450° C. to about 650° C. to produce a dried solid; and c) grinding said dried solid to produce said catalyst.

In yet another embodiment of the present invention, a method of preparing a catalyst is provided. The method comprises the following steps: a) combining $K_2HPO_4$, $Ba(NO_3)_2$, and $H_3PO_4$ to form a mixture, wherein the molar ratio of $Ba(NO_3)_2$, $K_2HPO_4$, and $H_3PO_4$ is about 3:1:4; b) calcining said mixture at about 450° C. to about 650° C. to produce a dried solid; c) grinding said dried solid to produce a ground solid; and d) contacting said ground solid with a gaseous mixture comprising water and lactic acid at a temperature of about 375° C. and a total pressure of about 10 barg to about 25 barg to produce said catalyst, and wherein the partial pressure of water in said gaseous mixture is about 3.5 bar to about 13 bar.

In one embodiment of the present invention, a process for converting lactic acid, lactic acid derivatives, or mixtures thereof to acrylic acid, acrylic acid derivatives, or mixtures thereof is provided. The process comprises the following steps: a) providing an aqueous solution comprising lactic acid, lactic acid derivatives, or mixtures thereof, wherein said lactic acid is in monomeric form in said aqueous solution; b) combining said aqueous solution with an inert gas to form an aqueous solution/gas blend; c) evaporating said aqueous solution/gas blend to produce a gaseous mixture; and d) dehydrating said gaseous mixture by contacting said gaseous mixture with a dehydration catalyst under a water partial pressure of about 10 psi (0.7 bar) or more, producing said acrylic acid, acrylic acid derivatives, or mixtures thereof.

In another embodiment of the present invention, a process for converting lactic acid to acrylic acid is provided. The process comprises the following steps: a) diluting an about 88% lactic acid aqueous solution with water to form an about 20 wt % lactic acid aqueous solution; b) heating said about 20 wt % lactic acid aqueous solution at a temperature between about 95° C. to about 100° C. to remove oligomers of said lactic acid, producing a monomeric lactic acid aqueous solution comprising at least 95 wt % of said lactic acid in monomeric form based on the total amount of lactic acid; c) combining said monomeric lactic acid aqueous solution with nitrogen to form an aqueous solution/gas blend; d) evaporating said aqueous solution/gas blend in a reactor with inside surface of borosilicate glass at a GHSV of about 6,000 $h^{-1}$ to about 7,200 $h^{-1}$ at a temperature between about 300° C. to about 375° C. to produce a gaseous mixture comprising about 2.5 mol % lactic acid and about 50 mol % water; e) dehydrating said gaseous mixture in a reactor with inside surface of borosilicate glass at a GHSV of about 3,600 $h^{-1}$ at a temperature between about 350° C. to about 425° C. by contacting said mixture with a dehydration catalyst under a pressure of about 360 psig (24.8 barg), producing said acrylic acid; and f) cooling said acrylic acid to give an acrylic acid solution at a GHSV between about 360 $h^{-1}$ to about 36,000 $h^{-1}$.

A process for converting lactic acid, lactic acid derivatives, or mixtures thereof to acrylic acid, acrylic acid derivatives, or mixtures thereof is provided. The process comprises the following steps: a) providing a solution comprising lactic acid, lactic acid derivatives, or mixtures thereof; b) combining the solution with a gas to form a solution/gas blend; and c) dehydrating the solution/gas blend by contacting the solution/gas blend with a dehydration catalyst.

A process for isomerization of lactic acid, lactic acid derivatives, or mixtures thereof into 3-hydroxypropionic acid, 3-hydroxypropionic acid derivatives, or mixtures thereof is provided. The process comprises contacting: a) lactic acid, lactic acid derivatives, or mixtures thereof; b) water; and c) a catalyst, comprising: i) phosphate anions described by formulae: $[H_{(1-\beta)}P_{(1+\beta)}O_{(4+3\beta)}]^{2(1+\beta)-}$ and $[H_{(2-2\gamma)}PO_{(4-\gamma)}]_{(1+(n-1)\gamma)}^{(1+(n-1)\gamma)-}$; and ii) at least two different cations, wherein the catalyst is neutrally charged, wherein β and γ are greater or equal to 0 and less or equal to 1, wherein n is at least 2, and wherein the molar ratio of said phosphate anions in the catalyst is between about 0.1 and about 10.

A process for converting lactic acid, lactic acid derivatives, or mixtures thereof to acrylic acid, acrylic acid derivatives, or mixtures thereof is provided. The process comprises the following steps: a) providing a solution comprising lactic acid, lactic acid derivatives, or mixtures thereof, wherein said lactic acid is in monomeric form in said solution; and b) dehydrating said lactic acid, lactic acid derivatives, or mixtures thereof by contacting said solution with a dehydration catalyst; wherein during said dehydration all the major components of said aqueous solution are in the liquid phase, producing said acrylic acid, acrylic acid derivatives, or mixtures thereof.

DETAILED DESCRIPTION OF THE INVENTION

I Definitions

As used herein, the term "bio-based" material refers to a renewable material.

As used herein, the term "renewable material" refers to a material that is produced from a renewable resource.

As used herein, the term "renewable resource" refers to a resource that is produced via a natural process at a rate comparable to its rate of consumption (e.g., within a 100 year time frame). The resource can be replenished naturally, or via agricultural techniques. Non-limiting examples of renewable resources include plants (e.g., sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Natural resources, such as crude oil, coal, natural gas, and peat, which take longer than 100 years to form, are not considered renewable resources. Because at least part of the material of the invention is derived from a renewable resource, which can sequester carbon dioxide, use of the material can reduce global warming potential and fossil fuel consumption.

As used herein, the term "petroleum-based" material refers to a material that is produced from fossil material, such as petroleum, natural gas, coal, etc.

As used herein, the term "condensed phosphate" refers to any salts containing one or several P—O—P bonds generated by corner sharing of $PO_4$ tetrahedra.

As used herein, the term "cyclophosphate" refers to any cyclic condensed phosphate constituted of two or more corner-sharing $PO_4$ tetrahedra.

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "oligophosphate" refers to any polyphosphates that contain five or less $PO_4$ units.

As used herein, the term "polyphosphate" refers to any condensed phosphates containing linear P—O—P linkages by corner sharing of $PO_4$ tetrahedra leading to the formation of finite chains.

As used herein, the term "ultraphosphate" refers to any condensed phosphate where at least two $PO_4$ tetrahedra of the anionic entity share three of their corners with the adjacent ones.

As used herein, the term "cation" refers to any atom or group of covalently-bonded atoms having a positive charge.

As used herein, the term "monovalent cation" refers to any cation with a positive charge of +1.

As used herein, the term "polyvalent cation" refers to any cation with a positive charge equal or greater than +2.

As used herein, the term "anion" refers to any atom or group of covalently-bonded atoms having a negative charge.

As used herein, the term "heteropolyanion" refers to any anion with covalently bonded $XO_p$ and $YO_r$ polyhedra, and thus includes X—O—Y and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the terms "LA" refers to lactic acid, "AA" refers to acrylic acid, "AcH" refers to acetaldehyde, and "PA" refers to propionic acid.

As used herein, the term "particle span" refers to a statistical representation of a given particle sample and is equal to $(D_{v,0.90} - D_{v,0.10})/D_{v,0.50}$. The term "median particle size" or $D_{v,0.50}$ refers to the diameter of a particle below which 50% of the total volume of particles lies. Further, $D_{v,0.10}$ refers to the particle size that separates the particle sample at the 10% by volume fraction and $D_{v,0.90}$, is the particle size that separates the particle sample at the 90% by volume fraction.

As used herein, the term "conversion" in % is defined as [lactic acid, lactic acid derivatives, or mixtures thereof flow rate in (mol/min)–lactic acid, lactic acid derivatives, or mixtures thereof flow rate out (mol/min)]/[lactic acid, lactic acid derivatives, or mixtures thereof flow rate in (mol/min)]×100. For the purposes of this invention, the term "conversion" means molar conversion, unless otherwise noted.

As used herein, the term "yield" in % is defined as [product flow rate out (mol/min)/lactic acid, lactic acid derivatives, or mixtures thereof flow rate in (mol/min)]×100. For the purposes of this invention, the term "yield" means molar yield, unless otherwise noted.

As used herein, the term "selectivity" in % is defined as [Yield/Conversion]×100. For the purposes of this invention, the term "selectivity" means molar selectivity, unless otherwise noted.

As used herein, the term "total carbon balance" is defined as: [((mol carbon monoxide out+mol carbon dioxide out+mol methane out)+(2×(mol acetic acid out+mol acetaldehyde out+mol ethane out+mol ethylene out))+(3×(mol acrylic acid out+mol propionic acid out+mol lactic acid out+mol hydroxyacetone out)+(5×mol 2,3 pentanedione out)+(6×mol acrylic acid dimer out))/(3×mol lactic acid in)]×100. If lactic acid derivative is used instead of lactic acid, the above formula needs to be adjusted according to the number of carbon atoms in the lactic acid derivative.

As used herein, the term "Gas Hourly Space Velocity" or "GHSV" in $h^{-1}$ is defined as 60×[Total gas flow rate (mL/min)/catalyst bed volume (mL)]. The total gas flow rate is calculated under Standard Temperature and Pressure conditions (STP; 0° C. and 1 atm).

As used herein, the term "Liquid Hourly Space Velocity" or "LHSV" in $h^{-1}$ is defined as 60×[Total liquid flow rate (mL/min)/catalyst bed volume (mL)].

As used herein, the term "antioxidant" refers to a molecule capable of terminating radical chain processes by either donating a hydrogen atom or the reaction of an olefinic bond to form a stabilized organic radical and thus terminate radical chain processes. Non limiting examples of antioxidants include thiols, polyphenols, butylated hydroxyl toluene (BHA), and butylated hydroxyl anisole (BHA).

As used herein, the term "catalyst" refers to either the pre-reaction or in-situ catalyst. The pre-reaction catalyst is the catalyst loaded into the chemical reactor, and the in-situ catalyst is the catalyst present in the reactor during the reaction. In general, a catalyst increases the reaction rate without being consumed in the reaction. Finally, the pre-reaction catalyst can remain unchanged during the reaction or undergo in-situ physical or chemical transformations during the reaction that can change its physical and chemical properties and become in-situ catalyst.

II Catalysts for the Conversion of Lactic Acid or its Derivatives to Acrylic Acid or its Derivatives Unexpectedly, it has been found that catalysts containing mixed monophosphate anions or mixed condensed phosphate anions dehydrate lactic acid, lactic acid derivatives, or mixtures thereof to acrylic acid, acrylic acid derivatives, or mixtures thereof with high: 1) yield and selectivity for acrylic acid, acrylic acid derivatives, or mixtures thereof, i.e., low amount and few side products; 2) efficiency, i.e., performance in short residence time; and 3) longevity. Although not wishing to be bound by any theory, applicants hypothesize that the catalyst, which includes at least monohydrogen monophosphate and dihydrogen monophosphate anions and two different cations or at least one condensed phosphate anion and two different cations, works as follows. The carboxylate group of the lactic acid, lactic acid derivatives, or mixtures thereof, associates with one or several cations, which in one embodiment is polyvalent, through one or both oxygen atoms, holding the molecule onto the surface of the catalyst, deactivating it from decarbonylation, and activating the C—OH bond for elimination. Then, the dihydrogen monophosphate anion(s), and/or the resulting protonated monophosphate anion(s), and/or the resulting condensed phosphate anion(s) dehydrate the lactic acid, lactic acid derivatives, or mixtures thereof by concerted protonation of the hydroxyl group, removal of a proton from the methyl group, and elimination of the protonated hydroxyl group as a molecule of water, generating acrylic acid, acrylic acid derivatives, or mixtures thereof and reactivating the catalyst. Also, applicants believe that a specific protonation state of the monophosphate anions or condensed phosphate anion is important to facilitate the dehydration of lactic acid, lactic acid derivatives, or mixtures thereof. Furthermore, applicants believe that when the lactic acid, lactic acid derivatives, or mixtures thereof are diluted with water, some condensed phosphate salts in the catalyst can be hydrolyzed to uncondensed monophosphates or shorter condensed phosphates, which, under the proper temperature and pressure conditions, facilitate the dehydration of lactic acid, lactic acid derivatives, or mixtures thereof.

In one embodiment of the present invention, the catalyst includes: (a) monohydrogen monophosphate and dihydrogen monophosphate anions described by formulae (Ia) and (IIa):

$$[HPO_4]^{2-} \quad (Ia)$$

and $$[H_2PO_4]^- \quad (IIa),$$

and (b) at least two different cations, wherein the catalyst is neutrally charged; and wherein the molar ratio of said monohydrogen monophosphate anion to said dihydrogen monophosphate anion in the catalyst is between about 0.1 and about 10. In another embodiment of the present invention, the molar ratio of monohydrogen monophosphate anion to dihydrogen monophosphate anion is between about 0.2 and about 5. In yet another embodiment of the present invention, the molar ratio of monohydrogen monophosphate anion to dihydrogen monophosphate anion is between about 0.25 and about 4. In even yet another embodiment of the present invention, the molar ratio of monohydrogen monophosphate anion to dihydrogen monophosphate anion is about 1.

In one embodiment of the present invention, the catalyst includes the monophosphate salts described by the formulae (Ib) and (IIb):

$$M^{II}HPO_4 \quad (Ib)$$

and $$M^{I}H_2PO_4 \quad (IIb),$$

wherein $M^I$ is one or more monovalent cation(s) and $M^{II}$ is one or more divalent cation(s). In another embodiment of the present invention, the molar ratio of $M^{II}HPO_4$ to $M^{I}H_2PO_4$ is between about 0.1 and about 10. In yet another embodiment of the present invention, the molar ratio of $M^{II}HPO_4$ to $M^{I}H_2PO_4$ is between about 0.2 and about 5. In even yet another embodiment of the present invention, the molar ratio of monohydrogen monophosphate anion to dihydrogen monophosphate anion is between about 0.25 and about 4. In one embodiment of the present invention, the molar ratio of $M^{II}HPO_4$ to $M^{I}H_2PO_4$ is about 1. In another embodiment of the present invention, $M^{II}HPO_4$ is substituted by $M^{III}M^{I}(HPO_4)_2$, where $M^{III}$ is one or more trivalent cation(s).

In another embodiment of the present invention, the catalyst includes the monophosphate salts described by the formulae (IIIa) and (IVa):

$$M^{II}_2P_2O_7 \quad (IIIa)$$

and $$(M^{I}PO_3)_n \quad (IVa),$$

wherein $M^I$ is one or more monovalent cation(s) and $M^{II}$ is one or more divalent cation(s), and wherein n is at least 2. In yet another embodiment of the present invention, the molar ratio of $M^{II}_2P_2O_7$ to $(M^{I}PO_3)_n$ is between about 0.1 and about 10. In one embodiment of the present invention, the molar ratio of $M^{II}_2P_2O_7$ to $(M^{I}PO_3)_n$ is between about 0.2 and about 5. In another embodiment of the present invention, the molar ratio of $M^{II}_2P_2O_7$ to $(M^{I}PO_3)_n$ is about 1. In yet another embodiment of the present invention, $M^{II}_2P_2O_7$ is substituted by $M^{III}M^{I}_2P_2O_7$, wherein $M^{III}$ is one or more trivalent cation(s).

In yet another embodiment of the present invention, the catalyst includes the monophosphate salts described by the formulae (Ib) and (IVa):

$$M^{II}HPO_4 \quad (Ib)$$

and $$(M^{I}PO_3)_n \quad (IVa),$$

wherein $M^I$ is one or more monovalent cation(s) and $M^{II}$ is one or more divalent cation(s), and wherein n is at least 2. In one embodiment of the present invention, the molar ratio of $M^{II}HPO_4$ to $(M^{I}PO_3)_n$ is between about 0.1 and about 10. In another embodiment of the present invention, the molar ratio of $M^{II}HPO_4$ to $(M^{I}PO_3)_n$ is between about 0.2 and about 5. In another embodiment of the present invention, the molar ratio of $M^{II}HPO_4$ to $(M^{I}PO_3)$ is between about 0.25 and about 4. In one embodiment of the present invention, the molar ratio of $M^{II}HPO_4$ to $(M^{I}PO_3)_n$ is about 1. In a another embodiment of the present invention, $M^{II}HPO_4$ is substituted by $M^{III}M^{I}(HPO_4)_2$, wherein $M^{III}$ is one or more trivalent cation(s).

In one embodiment of the present invention, the catalyst includes the monophosphate salts described by the formulae (IIIa) and (IIb):

$$M^{II}_2P_2O_7 \quad (IIIa)$$

and $$M^{I}H_2PO_4 \quad (IIb),$$

wherein $M^I$ is one or more monovalent cation(s) and $M^{II}$ is one or more divalent cation(s). In another embodiment of the present invention, the molar ratio of $M^{II}_2P_2O_7$ to $M^{I}H_2PO_4$ is between about 0.1 and about 10. In yet another embodiment of the present invention, the molar ratio of $M^{II}_2P_2O_7$ to $M^{I}H_2PO_4$ is between about 0.2 and about 5. In even yet another embodiment of the present invention, the molar ratio of $M^{II}{}_2P_2O_7$ to $M^IH_2PO_4$ is between about 0.25 and about 4. In one embodiment of the present invention, the molar ratio of $M^{II}{}_2P_2O_7$ to $M^IH_2PO_4$ is about 1. In another embodiment of the present invention, $M^{II}{}_2P_2O_7$ is substituted by $M^{III}M^IP_2O_7$, wherein $M^{III}$ is one or more trivalent cation(s).

In another embodiment of the present invention, the catalyst includes a phosphate salt described by the formula (III):

$$M^{II}{}_{2-\alpha}M_\alpha{}^I H_\alpha(H_{(1-\delta)}P_{(1+\delta)}O_{(4+3\delta)})_{(2-\delta)} \quad (III),$$

wherein $M^I$ is one or more monovalent cation(s) and $M^{II}$ is one or more divalent cation(s), wherein $\alpha$ is greater than about 0.2 and smaller than about 1.8, and wherein $\delta$ is either between 0 and about 1, or 0, or about 1. In one embodiment of the present invention, $\alpha$ is about 1. In another embodiment of the present invention, $\delta$ is about 1. In another embodiment of the present invention, $\delta$ is 0.

In yet another embodiment of the present invention, the catalyst includes a monophosphate salt described by the formula (IV):

$$M^{II}{}_{2-\alpha}M^I{}_\alpha H_\alpha(HPO_4)_2 \quad (IV),$$

wherein $M^I$ is one or more monovalent cation(s) and $M^{II}$ is one or more divalent cation(s); and wherein $\alpha$ is greater than about 0.2 and smaller than about 1.8. In one embodiment of the present invention, $\alpha$ is about 1.

In another embodiment of the present invention, the catalyst includes a condensed phosphate salt described by the formula (V):

$$M^{II}{}_{2-\alpha}M^I{}_\alpha H_\alpha P_2O_7 \quad (V),$$

wherein $M^I$ is one or more monovalent cation(s) and $M^{II}$ is one or more divalent cation(s); and wherein $\alpha$ is greater than about 0.2 and smaller than about 1.8. In yet another embodiment of the present invention, $\alpha$ is about 1.

In yet another embodiment of the present invention, the catalyst includes a phosphate salts described by the formula (IIIb):

$$M^{III}{}_{1-\alpha}M^I{}_{1+\alpha}H_\alpha(H_{(1-\delta)}P_{(1+\delta)}O_{(4+3\delta)})_{(2-\delta)} \quad (IIIb),$$

wherein $M^I$ is one or more monovalent cation(s) and $M^{III}$ is one or more trivalent cation(s), wherein $\alpha$ is greater than about 0.2 and smaller than about 1.8, and wherein $\delta$ is either between 0 and about 1, or 0, or about 1. In one embodiment of the present invention, $\alpha$ is about 1. In another embodiment of the present invention, $\delta$ is about 1. In another embodiment of the present invention, $\delta$ is 0.

In one embodiment of the present invention, the catalyst comprises: (a) the phosphate anions described by formulae (Ic) and (IIc):

$$[H_{(1-\beta)}P_{(1+\beta)}O_{(4+3\beta)}]^{2(1+\beta)-} \quad (Ic)$$

and $$[H_{(2-2\gamma)}PO_{(4-\gamma)}]_{(1+(n-1)\gamma)}{}^{(1+(n-1)\gamma)-} \quad (IIc),$$

and (b) at least two different cations, wherein the catalyst is neutrally charged, wherein $\beta$ and $\gamma$ are greater or equal to 0 and less or equal to 1, and wherein n is at least 2, and wherein the molar ratio of said phosphate anions in said catalyst is between about 0.1 and about 10. In another embodiment of the present invention, the molar ratio of said phosphate anions in said catalyst is between about 0.2 and about 5. In yet another embodiment of the present invention, the molar ratio of said phosphate anions in said catalyst is between about 0.25 and about 4. In even yet another embodiment of the present invention, the molar ratio of said phosphate anions in said catalyst is about 1.

In one embodiment of the present invention, $\beta$ and $\gamma$ are equal to 0 in formulae (Ic) and (IIc). In another embodiment of the present invention, $\beta$ and $\gamma$ are equal to 1 in formulae (Ic) and (IIc). In yet another embodiment of the present invention, $\beta$ is equal to 0 in formula (Ic) and $\gamma$ is equal to 1 in formula (IIc). In one embodiment of the present invention, $\beta$ is equal to 1 in formula (Ic) and $\gamma$ is equal to 1 in formula (IIc).

In another embodiment of the present invention, the catalyst comprises: (a) at least one condensed phosphate anion selected from the group consisting of formulae (VI), (VII), and (VIII):

$$[P_nO_{3n+1}]^{(n+2)-} \quad (VI),$$

$$[P_nO_{3n}]^{n-} \quad (VII),$$

and $$[P_{(2m+n)}O_{(5m+3n)}]^{n-} \quad (VIII),$$

and (b) at least two different cations, wherein n is at least 2 and m is at least 1, wherein the catalyst is neutrally charged, and wherein the molar ratio of phosphorus to the at least two different cations is between about 0.7 and about 1.7. The anions defined by formulae (VI), (VII), and (VIII) are also referred to as polyphosphates (or oligophosphates), cyclophosphates, and ultraphosphates, respectively.

In yet another embodiment of the present invention, the catalyst comprises: (a) at least two condensed phosphate anions selected from the group consisting of formulae (VI) and (VII):

$$[P_nO_{3n+1}]^{(n+2)-} \quad (VI),$$

and $$[P_nO_{3n}]^{n-} \quad (VII),$$

wherein n is at least 2, and (b) at least two different cations, wherein the catalyst is neutrally charged, and wherein the molar ratio of phosphorus to the at least two different cations is between about 0.7 and about 1.7.

In one embodiment of the present invention, the molar ratio of phosphorus to the cations in the catalyst is between about 0.7 and about 1.7. In another embodiment of the present invention, the molar ratio of phosphorus to the cations in the catalyst is between about 0.8 and about 1.3. In yet another embodiment of the present invention, the molar ratio of phosphorus to the cations in the catalyst is about 1.

In one embodiment of the present invention, the at least two different cations comprise: (a) at least one monovalent cation, and (b) at least one polyvalent cation. In another embodiment of the present invention, the molar ratio of the monovalent cations to the polyvalent cations is between about 0.1 and about 10. In yet another embodiment of the present invention, the molar ratio of the monovalent cations to the polyvalent cations is between about 0.25 and about 4. In one embodiment of the present invention, the molar ratio of the monovalent cations to the polyvalent cations is about 1.

In another embodiment of the present invention, the polyvalent cation is selected from the group consisting of divalent cations, trivalent cations, tetravalent cations, pentavalent cations, and mixtures thereof. Non-limiting examples of monovalent cations are $H^+$, $Li^+$, $Na^+$, $K^+$, $Rb^+$, $Cs^+$, $Tl^+$, and mixtures thereof. In yet another embodiment of the present invention, the monovalent cation is selected from the group consisting of Li$^+$, Na$^+$, K$^+$, Rb$^+$, Cs$^+$, and mixtures thereof; in another embodiment of the present invention, the monovalent cation is K$^+$ or Rb$^+$ or Cs$^+$. In one embodiment of the present invention, the monovalent cation is K$^+$. Non-limiting examples of polyvalent cations are cations of the alkaline earth metals (i.e., Be, Mg, Ca, Sr, Ba, and Ra), transition metals (e.g. Y, Ti, Zr, V, Nb, Cr, Mo, and Mn), poor metals (e.g. Zn, Ga, Si, Ge, B, Al, In, Sb, Sn, Bi, and Pb), lanthanides (e.g. La, Ce, Pr, Nd, Sm, Eu, Gd, Tb, Dy, Ho, Er, Tm, Yb, and Lu), and actinides (e.g. Ac and Th). In another embodiment of the present invention, the polyvalent cation is selected from the group consisting of the cations of the metals Be, Mg, Ca, Sr, Ba, Sc, Y, Ti, Zr, V, Nb, Cr, Mo, Mn, Ga, Si, Ge, B, Al, In, Tl, Sb, Sn, Bi, Pb, La, Ce, Er, and mixtures thereof. In yet another embodiment of the present invention, the polyvalent cation is selected from the group consisting of Be$^{2+}$, Mg$_{2+}$, Ca$^{2+}$, Sr$^{3+}$, Ba$^{2+}$, Mn$^{2+}$, Sn$^{2+}$, Pb$^{2+}$, Ti$^{3+}$, Cr$^{3+}$, Mn$^{3+}$, Al$^{3+}$, Ga$^{3+}$, Y$^{3+}$, In$^{3+}$, Sb$^{3+}$, Bi$^{3+}$, Er$^{3+}$, Si$^{4+}$, Ti$^{4+}$, V$^{4+}$, Ge$^{4+}$, Mo$^{4+}$, V$^{5+}$, Nb$^{5+}$, Sb$^{5+}$, and mixtures thereof. In one embodiment of the present invention, the polyvalent cation is selected from the group consisting of Ca$^{2+}$, Ba$^{2+}$, Mn$^{2+}$, Mn$^{3+}$, Mg$^{2+}$, Sr$^{2+}$, Y$^{3+}$, Al$^{3+}$, Er$^{3+}$, and mixtures thereof. In another embodiment of the present invention, the polyvalent cation is selected from the group consisting of Ca$^{2+}$, Ba$^{2+}$, Mn$^{3+}$, and mixtures thereof. In yet another embodiment of the present invention, the polyvalent cation is Ba$^{2+}$.

The catalyst can include cations: (a) H$^+$, Li$^+$, Na$^+$, K$^+$, Rb$^+$, Cs$^+$, or mixtures thereof; and (b) Be$^{2+}$, Mg$_{2+}$, Ca$^{2+}$, Sr$^{3+}$, Ba$^{2+}$, Mn$^{2+}$, Sn$^{2+}$, Pb$^{2+}$, Ti$^{3+}$, Cr$^{3+}$, Mn$^{3+}$, Al$^{3+}$, Ga$^{3+}$, Y$^{3+}$, In$^{3+}$, Sb$^{3+}$, Bi$^{3+}$, Er$^{3+}$, Si$^{4+}$, Ti$^{4+}$, V$^{4+}$, Ge$^{4+}$, Mo$^{4+}$, V$^{5+}$, Nb$^{5+}$, Sb$^{5+}$, or mixtures thereof. In one embodiment of the present invention, the catalyst comprises K$^+$ or Rb$^+$ or Cs$^+$ as monovalent cation, and Ca$^{2+}$, Ba$^{2+}$, or Mn$^{3+}$ as polyvalent cation. In yet another embodiment of the present invention, the catalyst comprises K$^+$ as the monovalent cation and Ba$^{2+}$ as the polyvalent cation.

In one embodiment of the present invention, the catalyst comprises Ba$_{2-x-s}$K$_{2x}$H$_{2s}$P$_2$O$_7$ and (K$_{(1-\zeta)}$Ba$_{\zeta/2}$PO$_3$)$_n$, wherein x, ζ, and s are greater or equal to 0 and less than about 0.5, and n is a positive integer. In another embodiment of the present invention, the catalyst comprises Ca$_{2-x-s}$K$_{2x}$H$_{2s}$P$_2$O$_7$ and (K$_{(1-\zeta)}$Ca$_{\zeta/2}$PO$_3$)$_n$, wherein x, ζ, and s are greater or equal to 0 and less than about 0.5, and n is a positive integer. In yet another embodiment of the present invention, the catalyst comprises Mn$_{1-x-s}$K$_{1+3x}$H$_{3s}$P$_2$O$_7$ and (K$_{(1-\zeta)}$Mn$_{\zeta/3}$PO$_3$)$_n$ wherein x, ζ, and s are greater or equal to 0 and less than about 0.5, and n is a positive integer. In one embodiment of the present invention, the catalyst comprises Mn$_{1-x-s}$K$_{2+2x}$H$_{2s}$P$_2$O$_7$ and (K$_{(1-\zeta)}$Mn$_{\zeta/2}$PO$_3$)$_n$ wherein x, ζ, and s are greater or equal to 0 and less than about 0.5, and n is a positive integer. In another embodiment of the present invention, the catalyst comprises any blend of Ba$_{2-x-s}$K$_{2x}$H$_{2s}$P$_2$O$_7$, Ca$_{2-x-s}$K$_{2x}$H$_{2s}$P$_2$O$_7$, Mn$_{1-x-s}$K$_{1+3x}$H$_{3s}$P$_2$O$_7$ or Mn$_{1-x-s}$K$_{2+2x}$H$_{2s}$P$_2$O$_7$; and (KPO$_3$)$_n$, (K$_{(1-\zeta)}$Ba$_{\zeta/2}$PO$_3$)$_n$, (K$_{(1-\zeta)}$Ca$_{\zeta/2}$PO$_3$)$_n$, (K$_{(1-\zeta)}$Mn$_{\zeta/3}$PO$_3$)$_n$, or (K$_{(1-\zeta)}$Mn$_{\zeta/2}$PO$_3$)$_n$, wherein x, ζ, and s are greater or equal to 0 and less than about 0.5, and n is a positive integer.

In one embodiment of the present invention, the catalyst comprises: (a) at least two different condensed phosphate anions selected from the group consisting of formulae (VI), (VII), and (VIII):

$$[P_nO_{3n+1}]^{(n+2)-} \quad (VI),$$

$$[P_nO_{3n}]^{n-} \quad (VII),$$

and $$[P_{(2m+n)}O_{(5m+3n)}]^{n-} \quad (VIII),$$

wherein n is at least 2 and m is at least 1, and (b) one cation, wherein the catalyst is neutrally charged, and further, wherein the molar ratio of phosphorus to the cation is between about 0.5 and about 40. In another embodiment of the present invention, the molar ratio of phosphorus to the cation is between about t/2 and about t, wherein t is the charge of the cation.

The catalyst can include an inert support that is constructed of a material comprising silicates, aluminates, carbons, metal oxides, and mixtures thereof. Alternatively, the carrier is inert relative to the reaction mixture expected to contact the catalyst. In the context of the reactions expressly described herein, in one embodiment of the present invention, the carrier is a low surface area silica or zirconia. When present, the carrier represents an amount of about 5 wt % to about 98 wt %, based on the total weight of the catalyst. Generally, a catalyst that includes an inert support can be made by one of two exemplary methods: impregnation or co-precipitation. In the impregnation method, a suspension of the solid inert support is treated with a solution of a pre-catalyst, and the resulting material is then activated under conditions that will convert the pre-catalyst to a more active state. In the co-precipitation method, a homogenous solution of the catalyst ingredients is precipitated by the addition of additional ingredients.

In another embodiment of the present invention, the catalyst can be sulfate salts; phosphate salts; mixtures of sulfate and phosphate salts; bases; zeolites or modified zeolites; metal oxides or modified metal oxides; supercritical water, or mixtures thereof.

III Catalyst Preparation Methods

In one embodiment of the present invention, the method of preparing the catalyst includes mixing at least two different phosphorus containing compounds, wherein each said compound is described by one of the formulae (IX) to (XXX), or any of the hydrated forms of said formulae:

$$M^I_y(H_{3-y}PO_4) \quad (IX)$$

$$M^{II}_y(H_{3-y}PO_4)_2 \quad (X)$$

$$M^{III}_y(H_{3-y}PO_4)_3 \quad (XI)$$

$$M^{IV}_y(H_{3-y}PO_4)_4 \quad (XII)$$

$$(NH_4)_y(H_{3-y}PO_4) \quad (XIII)$$

$$M^{II}_a(OH)_b(PO_4)_c \quad (XIV)$$

$$M^{III}_d(OH)_e(PO_4)_f \quad (XV)$$

$$M^{II}M^{I}PO_4 \quad (XVI)$$

$$M^{III}M^{I}_3(PO_4)_2 \quad (XVII)$$

$$M^{IV}_2M^{I}(PO_4)_3 \quad (XVIII)$$

$$M^I_zH_{4-z}P_2O_7 \quad (XIX)$$

$$M^{II}_vH_{(4-2v)}P_2O_7 \quad (XX)$$

$$M^{IV}P_2O_7 \quad (XXI)$$

$$(NH_4)_zH_{4-z}P_2O_7 \quad (XXII)$$

$$M^{III}M^{I}P_2O_7 \quad (XXIII)$$

$$M^IH_w(PO_3)_{(1+w)} \quad (XXIV)$$

$$M^{II}H_w(PO_3)_{(2+w)} \quad (XXV)$$

$$M^{III}H_w(PO_3)_{(3+w)} \quad (XXVI)$$

$$M^{IV}H_w(PO_3)_{(4+w)} \quad (XXVII)$$

$$M^{II}{}_g M^{I}{}_h (PO_3)_i \quad (XXVIII)$$

$$M^{III}{}_j M^{I}{}_k (PO_3)_l \quad (XXIX)$$

$$P_2O_5 \quad (XXX)$$

wherein $M^I$ is a monovalent cation; wherein $M^{II}$ is a divalent cation; wherein $M^{III}$ is a trivalent cation; wherein $M^{IV}$ is a tetravalent cation; wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: 2a=b+3c, 3d=e+3f, i=2g+h, and l=3j+k are satisfied.

In another embodiment of the present invention, the method of preparing the catalyst includes heating the phosphorus containing compounds after mixing. In another embodiment of the present invention, the method of preparing the catalyst includes contacting the phosphorus containing compounds after mixing, with a gaseous mixture comprising water. In one embodiment of the present invention, the method of preparing the catalyst includes spray drying the phosphorus containing compounds after mixing.

In one embodiment of the present invention, the catalyst is prepared by the steps including mixing one or more phosphorus containing compounds of formula (IX), wherein y is equal to 1, and one or more phosphorus containing compounds of formula (X), wherein is equal to 2. In another embodiment of the present invention, the catalyst is prepared by the steps including mixing $M^I H_2 PO_4$ and $M^{II} HPO_4$. In one embodiment of the present invention, $M^I$ is $K^+$ and $M^{II}$ is $Ca^{2+}$, i.e., the catalyst is prepared by the steps including mixing $KH_2PO_4$ and $CaHPO_4$; or $M^I$ is K and $M^{II}$ is $Ba^{2+}$, i.e., the catalyst is prepared by the steps including mixing $KH_2PO_4$ and $BaHPO_4$.

In one embodiment of the present invention, the catalyst is prepared by the steps including mixing one or more phosphorus containing compound of formula (IX), wherein y is equal to 1, one or more phosphorus containing compounds of formula (XX), wherein v is equal to 2. In another embodiment of the present invention, the catalyst is prepared by the steps including mixing $M^I H_2 PO_4$ and $M^{II}{}_2 P_2 O_7$. In one embodiment of the present invention, $M^I$ is $K^+$ and $M^{II}$ is $Ca^{2+}$, i.e., the catalyst is prepared by the steps including mixing $KH_2PO_4$ and $Ca_2P_2O_7$; or $M^I$ is $K^+$ and $M^{II}$ is $Ba^{2+}$, i.e., the catalyst is prepared by the steps including mixing $KH_2PO_4$ and $Ba_2P_2O_7$.

In another embodiment of the present invention, the catalyst is prepared by the steps including mixing one or more phosphorus containing compounds of formula (X), wherein said y is equal to 2, and one or more phosphorus containing compound of formula (XXIV), wherein said w is equal to 0. In another embodiment of the present invention, the phosphorus containing compounds are $(KPO_3)_n$ and $BaHPO_4$ or $CaHPO_4$; wherein n is a positive integer.

In yet another embodiment of the present invention, the catalyst is prepared by the steps including mixing one or more phosphorus containing compounds of formula (XX), wherein said v is equal to 2, and one or more phosphorus containing compound of formula (XXIV), wherein said w is equal to 0. In another embodiment of the present invention, the phosphorus containing compounds are $(KPO_3)_n$ and $Ba_2P_2O_7$ or $Ca_2P_2O_7$; wherein n is a positive integer.

In another embodiment of the present invention, the molar ratio of phosphorus to the cations in the catalyst is between about 0.7 and about 1.7; in yet another embodiment of the present invention, the molar ratio of phosphorus to the cations in the catalyst is between about 0.8 and about 1.3; and in another embodiment of the present invention, the molar ratio of phosphorus to the cations in the catalyst is about 1.

In another embodiment of the present invention, the method of preparing the catalyst includes mixing (a) at least one phosphorus containing compound, wherein each said compound is described by one of the formulae (IX) to (XXX), or any of the hydrated forms of said formulae:

$$M^I{}_y(H_{3-y}PO_4) \quad (IX)$$

$$M^{II}{}_y(H_{3-y}PO_4)_2 \quad (X)$$

$$M^{III}{}_y(H_{3-y}PO_4)_3 \quad (XI)$$

$$M^{IV}{}_y(H_{3-y}PO_4)_4 \quad (XII)$$

$$(NH_4)_y(H_{3-y}PO_4) \quad (XIII)$$

$$M^{II}{}_a(OH)_b(PO_4)_c \quad (XIV)$$

$$M^{III}{}_d(OH)_e(PO_4)_f \quad (XV)$$

$$M^{II}M^I PO_4 \quad (XVI)$$

$$M^{III}M^I{}_3(PO_4)_2 \quad (XVII)$$

$$M^{IV}{}_2 M^I(PO_4)_3 \quad (XVIII)$$

$$M^I{}_z H_{4-z} P_2 O_7 \quad (XIX)$$

$$M^{II}{}_v H_{(4-2v)} P_2 O_7 \quad (XX)$$

$$M^{IV} P_2 O_7 \quad (XXI)$$

$$(NH_4)_z H_{4-z} P_2 O_7 \quad (XXII)$$

$$M^{III} M^I P_2 O_7 \quad (XXIII)$$

$$M^I H_w(PO_3)_{(1+w)} \quad (XXIV)$$

$$M^{II} H_w(PO_3)_{(2+w)} \quad (XXV)$$

$$M^{III} H_w(PO_3)_{(3+w)} \quad (XXVI)$$

$$M^{IV} H_w(PO_3)_{(4+w)} \quad (XXVII)$$

$$M^{II}{}_g M^I{}_h (PO_3)_i \quad (XXVIII)$$

$$M^{III}{}_j M^I{}_k (PO_3)_l \quad (XXIX)$$

$$P_2 O_5 \quad (XXX)$$

wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: 2a=b+3c, 3d=e+3f, i=2g+h, and l=3j+k are satisfied, and (b) at least one non-phosphorus containing compound selected from the group consisting of nitrate salts, carbonate salts, acetate salts, metal oxides, chloride salts, sulfate salts, and metal hydroxides, wherein each said compound is described by one of the formulae (XXXI) to (LV), or any of the hydrated forms of said formulae:

$$M^I NO_3 \quad (XXXI)$$

$$M^{II}(NO_3)_2 \quad (XXXII)$$

| | |
|---|---|
| $M^{III}(NO_3)_3$ | (XXXVII) |
| $M^I_2CO_3$ | (XXXIV) |
| $M^{II}CO_3$ | (XXXV) |
| $M^{III}_2(CO_3)_3$ | (XXXVI) |
| $(CH_3COO)M^I$ | (XXXVII) |
| $(CH_3COO)_2M^{II}$ | (XXXVIII) |
| $(CH_3COO)_3M^{III}$ | (XXXIX) |
| $(CH_3COO)_4M^{IV}$ | (XL) |
| $M^I_2O$ | (XLI) |
| $M^{II}O$ | (XLII) |
| $M^{III}_2O_3$ | (XLIII) |
| $M^{IV}O_2$ | (XLIV) |
| $M^ICl$ | (XLV) |
| $M^{II}Cl_2$ | (XLVI) |
| $M^{III}Cl_3$ | (XLVII) |
| $M^{IV}Cl_4$ | (XLVIII) |
| $M^I_2SO_4$ | (XLIX) |
| $M^{II}_2SO_4$ | (L) |
| $M^{III}_2(SO_4)_3$ | (LI) |
| $M^{IV}_2(SO_4)_2$ | (LII) |
| $M^IOH$ | (LIII) |
| $M^{II}(OH)_2$ | (LIV) |
| $M^{III}_2(OH)_3$ | (LV). |

In another embodiment of the present invention, the method of preparing the catalyst includes heating the phosphorus containing compounds and the non-phosphorus containing compounds after mixing. In yet another embodiment of the present invention, the non-phosphorus containing compounds can be selected from the group consisting of carboxylic acid-derived salts, halide salts, metal acetylacetonates, and metal alkoxides.

In another embodiment of the present invention, the method of preparing the catalyst includes contacting the phosphorus containing and the non-phosphorus containing compounds after mixing, with a gaseous mixture comprising water. In one embodiment of the present invention, the method of preparing the catalyst includes spray drying the phosphorus containing and the non-phosphorus containing compounds after mixing.

In one embodiment of the present invention, the molar ratio of phosphorus to the cations in the catalyst is between about 0.7 and about 1.7; in another embodiment of the present invention, the molar ratio of phosphorus to the cations in the catalyst is between about 0.8 and about 1.3; and in yet another embodiment of the present invention, the molar ratio of phosphorus to the cations in the catalyst is about 1.

In another embodiment of the present invention, the catalyst is prepared by mixing and heating one or more phosphorus containing compounds of formulae (IX) to (XXX) or their hydrated forms, and one or more nitrate salts of formulae (XXXI) to (XXXIII) or their hydrated forms. In another embodiment of the present invention, the catalyst is prepared by mixing and heating one or more phosphorus containing compounds of formula (IX) and one or more nitrate salts of formula (XXXII). In a further embodiment of the present invention, the catalyst is prepared by mixing and heating a phosphorus containing compound of formula (IX) wherein y is equal to 2, a phosphorus containing compound of formula (IX) wherein y is equal to 0 (i.e., phosphoric acid), and a nitrate salt of formula (XXXII). In yet another embodiment of the present invention, the catalyst is prepared by mixing and heating $K_2HPO_4$, $H_3PO_4$, and $Ba(NO_3)_2$. In yet another embodiment of the present invention, the catalyst is prepared by mixing and heating $K_2HPO_4$, $H_3PO_4$, and $Ca(NO_3)_2$.

In one embodiment of the present invention, the catalyst is prepared by mixing and heating one or more phosphorus containing compounds of formula (IX) and one or more nitrate salts of formula (XXXIII). In a further embodiment of the present invention, the catalyst is prepared by mixing and heating a phosphorus containing compound of formula (IX) wherein y is equal to 2, a phosphorus containing compound of formula (IX) wherein y is equal to 0 (i.e., phosphoric acid), and a nitrate salt of formula (XXXIII). In yet another embodiment of the present invention, the catalyst is prepared by mixing and heating $K_2HPO_4$, $H_3PO_4$, and $Mn(NO_3)_2 \cdot 4H_2O$.

In one embodiment of the present invention, the catalyst is prepared by mixing and heating one or more phosphorus containing compounds of formula (X) and one or more nitrate salts of formula (XXXI). In another embodiment of the present invention, the catalyst is prepared by mixing and heating a phosphorus containing compound of formula (X) wherein y is equal to 2, a phosphorus containing compound of formula (X) wherein y is equal to 0 (i.e., phosphoric acid), and a nitrate salt of formula (XXXI). In yet another embodiment of the present invention, the catalyst is prepared by mixing and heating $BaHPO_4$, $H_3PO_4$, and $KNO_3$. In another embodiment of the present invention, the catalyst is prepared by mixing and heating $CaHPO_4$, $H_3PO_4$, and $KNO_3$.

In one embodiment of the present invention, the catalyst is prepared by mixing and heating one or more phosphorus containing compounds of formula (X), one or more phosphorus containing compounds of formula (XX), and one or more nitrate salts of formula (XXXI). In a further embodiment of the present invention, the catalyst is prepared by mixing and heating a phosphorus containing compound of formula (X), wherein y is equal to 0 (i.e., phosphoric acid); a phosphorus containing compound of formula (XX), wherein v is equal to 2; and a nitrate salt of formula (XXXI). In another embodiment of the present invention, the catalyst is prepared by mixing and heating $H_3PO_4$, $Ca_2P_2O_7$, and $KNO_3$. In yet another embodiment of the present invention, the catalyst is prepared by mixing and heating $H_3PO_4$, $Ba_2P_2O_7$, and $KNO_3$.

In another embodiment of the present invention, the catalyst is prepared by mixing and heating one or more phosphorus containing compounds of formula (XI) and one or more nitrate salts of formula (XXXI). In another embodiment of the present invention, the catalyst is prepared by mixing and heating a phosphorus containing compound of formula (XI), wherein y is equal to 3; a phosphorus containing compound of formula (XI), wherein y is equal to 0 (i.e., phosphoric acid); and a nitrate salt of formula (XXXI).

In yet another embodiment of the present invention, the catalyst is prepared by mixing and heating $MnPO_4 \cdot qH_2O$, $H_3PO_4$, and $KNO_3$.

In one embodiment of the present invention, the catalyst is prepared by mixing and heating one or more phosphorus containing compounds of formula (IX), one or more phosphorus containing compounds of formula (XIV), and one or more nitrate salts of formula (XXXII). In another embodiment of the present invention, the catalyst is prepared by mixing and heating a phosphorus containing compound of formula (IX), wherein y is equal to 2; a phosphorus containing compound of formula (IX), wherein y is equal to 0 (i.e., phosphoric acid); a phosphorus containing compound of formula (XIV), wherein a is equal to 2, b is equal to 1, and c is equal to 1; and a nitrate salt of formula (XXXII).

In one embodiment of the present invention, the catalyst is prepared by mixing and heating one or more phosphorus containing compounds of formula (X), one or more phosphorus containing compounds of formula (XIV), and one or more nitrate salts of formula (XXXI). In another embodiment of the present invention, the catalyst is prepared by mixing and heating a phosphorus containing compound of formula (X), wherein y is equal to 3; a phosphorus containing compound of formula (X), wherein y is equal to 0 (i.e., phosphoric acid); a phosphorus containing compound of formula (XIV), wherein a is equal to 2, b is equal to 1, and c is equal to 1; and a nitrate salt of formula (XXXI).

In one embodiment of the present invention, the catalyst is prepared by mixing and heating one or more phosphorus containing compounds described by one of the formulae (IX) to (XXX) or any of the hydrated forms, and one or more carbonate salts described by one of the formulae (XXXIV) to (XXXVI) or any of the hydrated forms.

In one embodiment of the present invention, the catalyst is prepared by mixing one or more phosphorus containing compounds described by one of the formulae (IX) to (XXX) or any of the hydrated forms, and one or more acetate salts described by one of the formulae (XXXVII) to (XL), any other organic acid-derived salts, or any of the hydrated forms.

In one embodiment of the present invention, the catalyst is prepared by mixing one or more phosphorus containing compounds described by one of the formulae (IX) to (XXX) or any of the hydrated forms, and one or more metal oxides described by one of the formulae (XLI) to (XLIV) or any of the hydrated forms.

In one embodiment of the present invention, the catalyst is prepared by mixing one or more phosphorus containing compounds described by one of the formulae (IX) to (XXX) or any of the hydrated forms, and one or more chloride salts described by one of the formulae (XLV) to (XLVIII), any other halide salts, or any of the hydrated forms.

In one embodiment of the present invention, the catalyst is prepared by mixing one or more phosphorus containing compounds described by one of the formulae (IX) to (XXX) or any of the hydrated forms, and one or more sulfate salts described by one of the formulae (XLIX) to (LII) or any of the hydrated forms.

In one embodiment of the present invention, the catalyst is prepared by mixing one or more phosphorus containing compounds described by one of the formulae (IX) to (XXX) or any of the hydrated forms, and one or more hydroxides described by one of the formulae (LIII) to (LV) or any of the hydrated forms.

In one embodiment of the present invention, the catalyst is prepared by mixing one or more phosphorus containing compounds of formulae (IX) to (XXX), and two or more non-phosphorus containing compounds of formulae (XXXI) to (LV) or their hydrated forms.

In one embodiment of the present invention, the method of preparing the catalyst includes contacting: (a) a gaseous mixture comprising water, with (b) a mixture of compounds containing (i) at least one condensed phosphate anion selected from the group consisting of formulae (VI) to (VIII):

$$[P_nO_{3n+1}]^{(n+2)-} \tag{VI}$$

$$[P_nO_{3n}]^{n-} \tag{VII}$$

and $$[P_{(2m+n)}O_{(5m+3n)}]^{n-} \tag{VIII},$$

and (ii) at least two different cations, wherein n is at least 2; wherein m is at least 1; wherein, said mixture of compounds is neutrally charged; and further, wherein the molar ratio of phosphorus to the cations in the catalyst is between about 0.7 and about 1.7. In another embodiment of the present invention, the molar ratio of phosphorus to the cations is about 1.

In yet another embodiment of the present invention, the catalyst is prepared by the steps including contacting: (a) a gaseous mixture comprising water, with (b) a mixture of compounds containing a condensed phosphate salt selected from the group consisting of $Ba_{2-x-s}K_{2x}H_{2s}P_2O_7$, $Ca_{2-x-s}K_{2x}H_{2s}P_2O_7$, $Mn_{1-x-s}K_{1+3x}H_{3s}P_2O_7$, $Mn_{1-x-s}K_{2+2x}H_{2s}P_2O_7$, and mixtures thereof; and $(KPO_3)_n$; wherein x and s are greater or equal to 0 and less than about 0.5 and n is at least 2.

In one embodiment of the present invention, the molar ratio of phosphorus to the cations (i.e. $M^I + M^{II} + M^{III} + \ldots$) is between about 0.7 and about 1.7; in another embodiment of the present invention, the molar ratio of phosphorus to the cations (i.e. $M^I + M^{II} + M^{III} + \ldots$) is between about 0.8 and about 1.3, and in yet another embodiment of the present invention, the molar ratio of phosphorus to the cations (i.e. $M^I + M^{II} + M^{III} + \ldots$) is about 1. For example, in an embodiment when the catalyst includes potassium ($K^+$) and barium ($Ba^{2+}$), the molar ratio between phosphorus and the metals (K+Ba) is between about 0.7 and about 1.7; and in another embodiment of the present invention, the molar ratio between phosphorus and the metals (K+Ba) is about 1.

In one embodiment of the present invention, the catalyst can include an inert support that is constructed of a material comprising silicates, aluminates, carbons, metal oxides, and mixtures thereof. Alternatively, the carrier is inert relative to the reaction mixture expected to contact the catalyst. In another embodiment of the present invention, the method of preparing the catalyst can further include mixing an inert support with the catalyst before, during, or after the mixing of the phosphorus containing compounds, wherein the inert support includes silicates, aluminates, carbons, metal oxides, and mixtures thereof. In yet another embodiment of the present invention, the method of preparing the catalyst can further include mixing an inert support with the catalyst before, during, or after the mixing of the phosphorus containing compounds and the non-phosphorus containing compounds, wherein the inert support includes silicates, aluminates, carbons, metal oxides, and mixtures thereof.

In one embodiment of the present invention, the method of preparing the catalyst includes mixing the phosphorus containing compounds with a surfactant. In another embodiment of the present invention, the method of preparing the catalyst includes mixing the phosphorus containing and the non-phosphorus containing compounds with a surfactant. In yet another embodiment of the preset invention, the surfactant is cationic or zwitterionic. Non-limiting examples of surfactants are myristyltrimethylammonium bromide, hexadecyltrimethylammonium bromide, dodecyltrimethylammonium bromide, decyltrimethylammonium bromide, and octadecyltrimethyl ammonium bromide.

Mixing of the phosphorus containing compounds or the phosphorus containing and non-phosphorus containing compounds of the catalyst can be performed by any method known to those skilled in the art, such as, by way of example and not limitation: solid mixing and co-precipitation. In the solid mixing method, the various components are physically mixed together with optional grinding using any method known to those skilled in the art, such as, by way of example and not limitation, shear, extensional, kneading, extrusion, and others. In the co-precipitation method, an aqueous solution or suspension of the various components, including one or more of the phosphate compounds, is prepared, followed by optional filtration and heating to remove solvents and volatile materials (e.g., water, nitric acid, carbon dioxide, ammonia, or acetic acid). In one embodiment of the present invention, the mixture of the phosphorus containing compounds or the mixture of the phosphorous and non-phosphorus containing compounds is heated after mixing. The heating is typically done using any method known to those skilled in the art, such as, by way of example and not limitation, convection, conduction, radiation, microwave heating, and others.

In one embodiment of the invention, the catalyst is calcined. Calcination is a process that allows chemical reaction and/or thermal decomposition and/or phase transition and/or removal of volatile materials. The calcination process is carried out with any equipment known to those skilled in the art, such as, by way of example and not limitation, furnaces or reactors of various designs, including shaft furnaces, rotary kilns, hearth furnaces, and fluidized bed reactors. The calcination temperature is, in one embodiment of the present invention, about 200° C. to about 1200° C.; in another embodiment of the present invention, the calcination temperature is about 250° C. to about 900° C.; in yet another embodiment of the present invention, the calcination temperature is about 450° C. to about 650° C.; and in even yet another embodiment of the present invention, the calcination temperature is about 300° C. to about 600° C. The calcination time is, in one embodiment of the present invention, about one hour to about seventy-two hours. In another embodiment, the calcination time is between about two hours and about twelve hours. In yet another embodiment, the calcination time is about four hours. In one embodiment, the heating ramp is about 0.5° C./min to about 20° C./min. In another embodiment, the heating ramp is about 10° C./min.

While many methods and machines are known to those skilled in the art for fractionating particles into discreet sizes and determining particle size distribution, sieving is one of the easiest, least expensive, and common ways. An alternative way to determine the size distribution of particles is with light scattering. Following calcination, the catalyst is, in one embodiment of the present invention, ground and sieved to provide a more uniform product. The particle size distribution of the catalyst particles includes a particle span that, in one embodiment of the present invention, is less than about 3; in another embodiment of the present invention, the particle size distribution of the catalyst particles includes a particle span that is less than about 2; and in yet another embodiment of the present invention, the particle size distribution of the catalyst particles includes a particle span that is less than about 1.5. In another embodiment of the present invention, the catalyst is sieved to a median particle size of about 50 µm to about 500 µm. In another embodiment of the present invention, the catalyst is sieved to a median particle size of about 100 µm to about 200 µm.

In one embodiment of the present invention, the method of preparing the catalyst includes molding the catalyst particles. Non-limiting examples of molding operations are granulation, agglomeration, compaction, pelleting, and extrusion.

In one embodiment of the present invention, the catalyst is prepared by the steps including: a) combining $BaHPO_4$ and $KH_2PO_4$ in a molar ratio between about 4:1 and about 1:4 to produce a solid mixture; and b) grinding said solid mixture to produce said catalyst as a mixed powder.

In another embodiment of the present invention, the catalyst is prepared by the steps including: a) combining $BaHPO_4$ and $KH_2PO_4$ in a molar ratio between about 4:1 and about 1:4 to produce a solid mixture; b) grinding said solid mixture to produce a mixed powder; and c) calcining said mixed powder between about 450° C. and about 650° C. to produce said catalyst as a condensed phosphate mixture.

In yet another embodiment of the present invention, the catalyst is prepared by the steps including: a) combining $BaHPO_4$ and $KH_2PO_4$ in a molar ratio between about 4:1 and about 1:4 to produce a solid mixture; b) grinding said solid mixture to produce a mixed powder; c) calcining said mixed powder between about 450° C. and about 650° C. to produce a condensed phosphate mixture; and d) contacting said condensed phosphate mixture with a gaseous mixture comprising water and lactic acid at a temperature of about 350° C. to about 400° C. and a total pressure of about 10 barg to about 25 barg to produce said catalyst, and wherein the partial pressure of water in said gaseous mixture is about 3.5 bar to about 13 bar.

In one embodiment of the present invention, the catalyst is prepared by the steps including: a) combining $MnPO_4.qH_2O$, $KNO_3$, and $H_3PO_4$, in a molar ratio of about 0.3:1:1, on an anhydrous basis, and water to produce a wet mixture, b) calcining said wet mixture at about 450° C. to about 650° C. to give a dried solid, and c) grinding and sieving said dried solid to produce said catalyst.

In another embodiment of the present invention, the catalyst is prepared by the steps including: a) combining $MnPO_4.qH_2O$, $KNO_3$, and $H_3PO_4$, in a molar ratio of about 0.3:1:1, on an anhydrous basis, and water to produce a wet mixture, b) calcining said wet mixture at about 450° C. to about 650° C. to give a dried solid, c) grinding and sieving said dried solid to produce a condensed phosphate mixture; and d) contacting said condensed phosphate mixture with a gaseous mixture comprising water and lactic acid at a temperature of about 350° C. to about 400° C. and a total pressure of about 10 barg to about 25 barg to produce said catalyst, and wherein the partial pressure of water in said gaseous mixture is about 3.5 bar to about 13 bar.

In yet another embodiment of the present invention, the catalyst is prepared by the steps including: a) combining $Ca_2P_2O_7$, $KNO_3$, and $H_3PO_4$, in a molar ratio of about 1.6:1:1, and water to produce a wet mixture, b) calcining said wet mixture at about 450° C. to about 650° C. to give a dried solid, and c) grinding and sieving said dried solid to produce said catalyst.

In another embodiment of the present invention, the catalyst is prepared by the steps including: a) combining a phosphorus containing compound, a nitrate salt, phosphoric acid, and solvent to produce a wet mixture, wherein the molar ratio between phosphorus and the cations in both the phosphorus containing compound and nitrate salt is about 1, b) calcining said wet mixture at about 450° C. to about 650° C. to produce a dried solid, and c) grinding and sieving said dried solid to produce said catalyst.

In yet another embodiment of the present invention, the catalyst is prepared by the steps including: a) combining a phosphorus containing compound, a nitrate salt, phosphoric acid, and solvent to produce a wet mixture, wherein the molar ratio between phosphorus and the cations in both the phosphorus containing compound and nitrate salt is about 1, b) grinding said wet mixture to produce a wet suspension, c) calcining said wet suspension at about 120° C., and about 450° C. to about 650° C. to produce a dried solid, and d) grinding and sieving said dried solid to produce said catalyst.

In one embodiment of the present invention, the solvent is selected from the group consisting of water, alcohols, ketones, ethers, hydrocarbons, or mixtures thereof. Non-limiting examples of alcohols are ethanol, n-propanol, iso-propanol, and n-butanol. A non-limiting example of ketones is acetone.

In another embodiment of the present invention, the catalyst is prepared by the steps including: a) combining $Ba(NO_3)_2$, $K_2HPO_4$, and $H_3PO_4$, in a molar ratio of about 3:1:4, and water to produce a wet mixture, b) heating said wet mixture to about 80° C. with stirring until near dryness to produce a wet solid, c) calcining said wet solid at about 450° C. to about 650° C. to give a dried solid, and d) grinding and sieving said dried solid to produce said catalyst.

In yet another embodiment of the present invention, the catalyst is prepared by the steps including: a) combining $K_2HPO_4$, $Ba(NO_3)_2$, $H_3PO_4$, and water to produce a wet mixture, wherein the molar ratio of $Ba(NO_3)_2$, $K_2HPO_4$, and $H_3PO_4$ is about 3:1:4; b) heating said wet mixture to about 80° C. with stirring until near dryness to produce a wet solid; c) calcining said wet solid at about 450° C. to about 650° C. to produce a dried solid; and d) contacting said dried solid with a gaseous mixture comprising water and lactic acid at a temperature of about 350° C. to about 400° C. and a total pressure of about 10 barg to about 25 barg to produce said catalyst, and wherein the partial pressure of water in said gaseous mixture is about 3.5 bar to about 13 bar.

In one embodiment of the present invention, the catalyst is prepared by the steps including: a) combining $K_2HPO_4$, $Ba(NO_3)_2$, and $H_3PO_4$ to form a mixture, wherein the molar ratio of $Ba(NO_3)_2$, $K_2HPO_4$, and $H_3PO_4$ is about 3:1:4; b) calcining said mixture at about 450° C. to about 650° C. to produce a dried solid; and c) grinding said dried solid to produce said catalyst.

In another embodiment of the present invention, the catalyst is prepared by the steps including: a) combining $K_2HPO_4$, $Ba(NO_3)_2$, and $H_3PO_4$ to form a mixture, wherein the molar ratio of $Ba(NO_3)_2$, $K_2HPO_4$, and $H_3PO_4$ is about 3:1:4; b) calcining said mixture at about 450° C. to about 650° C. to produce a dried solid; c) grinding said dried solid to produce a ground solid; and d) contacting said ground solid with a gaseous mixture comprising water and lactic acid at a temperature of about 375° C. and a total pressure of about 10 barg to about 25 barg to produce said catalyst, and wherein the partial pressure of water in said gaseous mixture is about 3.5 bar to about 13 bar.

In another embodiment of the present invention, the catalyst is prepared by the steps including: a) combining $Mn(NO_3)_2 \cdot 4H_2O$, $K_2HPO_4$, and $H_3PO_4$, in a molar ratio of about 1:1.5:2, and water to produce a wet mixture, b) heating said wet mixture to about 80° C. with stirring until near dryness to produce a wet solid, c) calcining said wet solid at about 450° C. to about 650° C. to produce a dried solid, and d) grinding and sieving said dried solid to produce said catalyst.

In yet another embodiment of the present invention, the catalyst is prepared by the steps including: a) combining $Ca_2P_2O_7$ and $KH_2PO_4$ in a molar ratio of about 1:3 to produce a solid mixture, and b) calcining said solid mixture at about 450° C. to about 650° C., to produce said catalyst.

Following calcination and optional grinding and sieving, the catalyst can be utilized to catalyze several chemical reactions. Non-limiting examples of reactions are: dehydration of lactic acid to acrylic acid (as described in further detail below); dehydration of 3-hydroxypropionic acid or 3-hydroxypropionic acid derivatives, or mixtures thereof to acrylic acid; dehydration of glycerin to acrolein; isomerization of lactic acid to 3-hydroxypropionic acid in the presence of water; reduction of lactic acid to propanoic acid or 1-propanol in the presence of hydrogen gas, dehydration of aliphatic alcohols to alkenes or olefins; dehydrogenation of aliphatic alcohols to ethers; other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

IV Methods of Producing Acrylic Acid, Acrylic Acid Derivatives, or Mixtures Thereof A method for dehydrating lactic acid, lactic acid derivatives, or mixtures thereof to acrylic acid, acrylic acid derivatives, or mixtures thereof is provided.

Alternative catalysts comprising anions selected from the group consisting of non-phosphorus-containing anions, heteropolyanions, and phosphate adducts, and at least two different cations, wherein the catalyst is neutrally charged, can be utilized for dehydrating lactic acid, lactic acid derivatives, or mixtures thereof to acrylic acid, acrylic acid derivatives, or mixtures thereof. Non-limiting examples of non-phosphorus-containing anions are arsenates, condensed arsenates, nitrates, sulfates, borates, carbonates, chromates, vanadates, niobates, tantalates, selenates, and other monomeric oxoanions or polyoxoanions that may be apparent to those having ordinary skill in the art. Non-limiting examples of heteropolyanions are heteropolyphosphates, such as arsenatophosphates, phosphoaluminates, phosphoborates, phosphocromates, phosphomolybdates, phosphosilicates, phosphosulfates, phosphotungstates, and others that may be apparent to those having ordinary skill in the art. Non-limiting examples of phosphate adducts are adducts of phosphate anions with telluric acid, halides, borates, carbonates, nitrates, sulfates, chromates, silicates, oxalates, mixtures thereof, or others that may be apparent to those having ordinary skill in the art.

Derivatives of lactic acid can be metal or ammonium salts of lactic acid, alkyl esters of lactic acid, lactic acid oligomers, cyclic di-esters of lactic acid, lactic acid anhydride, 2-alkoxypropoanoic acids or their alkyl esters, 2-aryloxypropanoic acids or their alkyl esters, 2-acyloxypropanoic acids or their alkyl esters, or a mixture thereof. Non-limiting examples of metal salts of lactic acid are sodium lactate, potassium lactate, and calcium lactate. Non-limiting examples of alkyl esters of lactic acid are methyl lactate, ethyl lactate, butyl lactate, 2-ethylhexyl lactate, or mixtures thereof. A non-limiting example of cyclic di-esters of lactic acid is dilactide. Non-limiting examples of 2-alkoxypropoanoic acids are 2-methoxypropanoic acid and 2-ethoxypropanoic acid. A non-limiting example of 2-aryloxypropanoic acid is 2-phenoxypropanoic acid. A non-limiting example of 2-acyloxypropanoic acid is 2-acetoxypropanoic acid.

Acrylic acid derivatives can be metal or ammonium salts of acrylic acid, alkyl esters of acrylic acid, acrylic acid oligomers, or mixtures thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

In one embodiment of the present invention, a method of making acrylic acid, acrylic acid derivatives, or mixtures thereof comprising contacting a stream comprising lactic acid, lactic acid derivatives, or mixtures thereof with any catalyst disclosed in Section II ("Catalysts for the Conversion of Lactic Acid or its Derivatives to Acrylic Acid or its Derivatives") of the present invention is provided.

The stream comprising lactic acid, lactic acid derivatives, or mixtures thereof can include a liquid stream and an inert gas (i.e., a gas otherwise inert to the reaction mixture under the conditions of the method) that can be separately or jointly fed into an evaporation vessel upstream of the catalyst reactor for the stream to become gaseous. The liquid stream can include the lactic acid, lactic acid derivatives, or mixtures thereof and a diluent. Non-limiting examples of the diluent are water, methanol, ethanol, acetone, C3 to C8 linear and branched alcohols, C5 to C8 linear and branched alkanes, ethyl acetate, non-volatile ethers (including diphenyl ether), and mixtures thereof. In one embodiment of the present invention, the diluent comprises water. In another embodiment of the present invention, the liquid stream comprises an aqueous solution of lactic acid or lactic acid derivatives selected from the group consisting of lactide, lactic acid oligomers, salts of lactic acid, 2-alkoxypropanoic acids or their alkyl esters, 2-aryloxypropanoic acids or their alkyl esters, 2-acyloxypropanoic acids or their alkyl esters, and alkyl lactates. In one embodiment of the present invention, the liquid stream includes between about 2 wt % to about 95 wt % lactic acid or lactic acid derivatives, based on the total weight of the liquid stream. In another embodiment of the present invention, the liquid steam includes between about 5 wt % to about 50 wt % lactic acid or lactic acid derivatives, based on the total weight of the liquid stream. In another embodiment of the present invention, the liquid stream includes between about 10 wt % to about 25 wt % lactic acid or lactic acid derivatives, based on the total weight of the liquid stream. In another embodiment of the present invention, the liquid stream includes about 20 wt % lactic acid or lactic acid derivatives, based on the total weight of the liquid stream. In another embodiment of the present invention, the liquid stream comprises an aqueous solution of lactic acid along with derivatives of lactic acid. In another embodiment of the present invention, the liquid stream comprises less than about 30 wt % of lactic acid derivatives, based on the total weight of the liquid stream. In another embodiment of the present invention, the liquid stream comprises less than about 10 wt % of lactic acid derivatives, based on the total weight of the liquid stream. In yet another embodiment of the present invention, the liquid stream comprises less than about 5 wt % of lactic acid derivatives, based on the total weight of the liquid stream.

The inert gas is a gas that is otherwise inert to the reaction mixture under the conditions of the method. Non-limiting examples of the inert gas are nitrogen, air, helium, argon, carbon dioxide, carbon monoxide, steam, and mixtures thereof. In one embodiment of the present invention, the inert gas is nitrogen.

The stream comprising lactic acid, lactic acid derivatives, or mixtures thereof can be in the form of a gaseous mixture when contacting the catalyst. In one embodiment of the present invention, the concentration of lactic acid, lactic acid derivatives, or mixtures thereof based on the total moles of said stream (calculated under STP conditions) is between about 0.5 mol % to about 50 mol %. In another embodiment of the present invention, the concentration of lactic acid, lactic acid derivatives, or mixtures thereof based on the total moles of said stream (calculated under STP conditions) is between about 1 mol % to about 10 mol %. In another embodiment of the present invention, the concentration of lactic acid, lactic acid derivatives, or mixtures thereof based on the total moles of said stream (calculated under STP conditions) is between about 1.5 mol % to about 3.5 mol %. In yet another embodiment of the present invention, the concentration of lactic acid, lactic acid derivatives, or mixtures thereof based on the total moles of said stream (calculated under STP conditions) is about 2.5 mol %.

In one embodiment of the present invention, the temperature at which said stream comprising lactic acid, lactic acid derivatives, or mixtures thereof contacts the catalyst is between about 120° C. and about 700° C. In another embodiment of the present invention, the temperature at which said stream comprising lactic acid, lactic acid derivatives, or mixtures thereof contacts the catalyst is between about 150° C. and about 500° C. In another embodiment of the present invention, the temperature at which said stream comprising lactic acid, lactic acid derivatives, or mixtures thereof contacts the catalyst is between about 300° C. and about 450° C. In yet another embodiment of the present invention, the temperature at which said stream comprising lactic acid, lactic acid derivatives, or mixtures thereof contacts the catalyst is between about 325° C. and about 400° C.

In one embodiment of the present invention, the stream comprising lactic acid, lactic acid derivatives, or mixtures thereof contacts the catalyst at a GHSV between about 720 $h^{-1}$ and about 36,000 $h^{-1}$. In another embodiment of the present invention, the stream comprising lactic acid, lactic acid derivatives, or mixtures thereof contacts the catalyst at a GHSV between about 1,800 $h^{-1}$ to about 7,200 $h^{-1}$. In another embodiment of the present invention, the stream comprising lactic acid, lactic acid derivatives, or mixtures thereof contacts the catalyst at a GHSV about 3,600 $h^{-1}$.

In one embodiment of the present invention, the stream comprising lactic acid, lactic acid derivatives, or mixtures thereof contacts the catalyst at a pressure between about 0 psig and about 550 psig (37.9 barg). In another embodiment of the present invention, the stream comprising lactic acid, lactic acid derivatives, or mixtures thereof contacts the catalyst at a pressure of about 360 psig (24.8 barg).

In one embodiment of the present invention, the diluent comprises water and the water partial pressure in the stream or gaseous mixture is about 10 psi (0.7 bar) or more. In another embodiment of the present invention, the diluent comprises water and the water partial pressure in the stream or gaseous mixture is between about 10 psi (0.7 bar) and about 500 psi (34.5 bar). In yet another embodiment of the present invention, the diluent comprises water and the water partial pressure in the stream or gaseous mixture is between about 15 psi (1 bar) and about 320 psi (22.1 bar). In even yet another embodiment of the present invention, the diluent comprises water and the water partial pressure in the stream or gaseous mixture is between about 50 psi (3.5 bar) and about 189 psi (13 bar). In one embodiment of the present invention, the diluent comprises water and the water partial pressure in the stream or gaseous mixture is about 189 psi (13 bar).

In one embodiment of the present invention, the stream comprising lactic acid, lactic acid derivatives, or mixtures thereof contacts the catalyst in a reactor having an interior surface comprising material selected from the group consisting of quartz, borosilicate glass, silicon, manufactured sapphire, and mixtures thereof. In another embodiment of the present invention, the stream comprising lactic acid, lactic acid derivatives, or mixtures thereof contacts the catalyst in a reactor having an interior surface comprising material selected from the group consisting of passivated hastelloy, passivated inconel, passivated stainless steel, and mixtures thereof. In another embodiment of the present invention, the stream comprising lactic acid, lactic acid derivatives, or mixtures thereof contacts the catalyst in a reactor having an interior surface comprising material selected from the group consisting of quartz or borosilicate glass. In another embodiment of the present invention, the stream comprising lactic acid, lactic acid derivatives, or mixtures thereof contacts the catalyst in a reactor having an interior surface comprising borosilicate glass.

In one embodiment of the present invention, the method includes contacting the catalyst with a gaseous mixture comprising lactic acid, lactic acid derivatives, or mixtures thereof under conditions sufficient to produce acrylic acid, acrylic acid derivatives, or mixtures thereof in a yield of at least 50%. In another embodiment of the present invention, the method includes contacting the catalyst with a gaseous mixture comprising lactic acid, lactic acid derivatives, or mixtures thereof under conditions are sufficient to produce acrylic acid, acrylic acid derivatives, or mixtures thereof in a yield of at least about 70%. In another embodiment of the present invention, the method includes contacting the catalyst with a gaseous mixture comprising lactic acid, lactic acid derivatives, or mixtures thereof under conditions are sufficient to produce acrylic acid, acrylic acid derivatives, or mixtures thereof in a yield of at least 80%. In another embodiment of the present invention, the method conditions are sufficient to produce acrylic acid, acrylic acid derivatives, or mixtures thereof with a selectivity of at least about 50%. In another embodiment of the present invention, the method conditions are sufficient to produce acrylic acid, acrylic acid derivatives, or mixtures thereof with a selectivity of at least about 70%. In another embodiment of the present invention, the method conditions are sufficient to produce acrylic acid, acrylic acid derivatives, or mixtures thereof with a selectivity of at least about 80%. In another embodiment of the present invention, the method conditions are sufficient to produce acrylic acid, acrylic acid derivatives, or mixtures thereof with propanoic acid as an impurity, wherein the propanoic acid selectivity is less than about 5%. In another embodiment of the present invention, the method conditions are sufficient to produce acrylic acid, acrylic acid derivatives, or mixtures thereof with propanoic acid as an impurity, wherein the propanoic acid selectivity is less than about 1%. In another embodiment of the present invention, the method conditions are sufficient to produce acrylic acid, acrylic acid derivatives, or mixtures thereof with a conversion of said lactic acid, lactic acid derivatives, or mixtures thereof of more than about 50%. In another embodiment of the present invention, the method conditions are sufficient to produce acrylic acid, acrylic acid derivatives, or mixtures thereof with a conversion of said lactic acid, lactic acid derivatives, or mixtures thereof of more than about 80%.

Among the benefits attainable by the foregoing embodiments is the low yield of side products. In one embodiment of the present invention, the conditions are sufficient to produce propionic acid in a yield of less than about 6% from lactic acid present in the gaseous mixture. In another embodiment of the present invention, the conditions are sufficient to produce propionic acid in a yield of less than about 1%, from lactic acid present in the gaseous mixture. In one embodiment of the present invention, the conditions are sufficient to produce each of acetic acid, pyruvic acid, 1,2-propanediol, hydroxyacetone, 3-hydroxypropanoic acid, acrylic acid dimer, and 2,3-pentanedione in a yield of less than about 2% from lactic acid present in the gaseous mixture. In another embodiment of the present invention, the conditions are sufficient to produce each of acetic acid, pyruvic acid, 1,2-propanediol, hydroxyacetone, 3-hydroxypropanoic acid, acrylic acid dimer, and 2,3-pentanedione in a yield of less than about 0.5%, from lactic acid present in the gaseous mixture. In one embodiment of the present invention, the conditions are sufficient to produce acetaldehyde in a yield of less than about 8% from lactic acid present in the gaseous mixture. In another embodiment of the present invention, the conditions are sufficient to produce acetaldehyde in a yield of less than about 4% from lactic acid present in the gaseous mixture. In another embodiment of the present invention, the conditions are sufficient to produce acetaldehyde in a yield of less than about 3%, from lactic acid present in the gaseous mixture. These yields are believed to be, heretofore, unattainably low. Yet, these benefits are indeed achievable as further evidenced in the Examples set out below.

In one embodiment of the present invention, a method of making acrylic acid is provided. The method comprises contacting: (a) a gaseous stream comprising: (i) lactic acid, (ii) water, and (iii) nitrogen, wherein said lactic acid is present in an amount of about 2.5 mol % and wherein said water is present in an amount of about 50 mol % based on the total moles of said gaseous stream, with (b) a catalyst comprising: (i) $Ba_{2-x-s}K_{2x}H_{2s}P_2O_7$; and (ii) $(K_{(1-\zeta)}Ba_{\zeta/2}PO_3)_n$; wherein x, s, and $\zeta$ are greater or equal to 0 and less than about 0.5 and n is a positive integer, wherein, said contacting of said gaseous stream with said catalyst is performed at a temperature of about 300° C. to about 450° C., at a GHSV of about 3,600 $h^{-1}$ and at a pressure of about 360 psig (24.8 barg), in a reactor having an interior surface comprising material selected from the group consisting of quartz and borosilicate glass, whereby acrylic acid is produced as a result of said lactic acid being contacted with said catalyst.

In another embodiment of the present invention, a method of making acrylic acid is provided. The method comprises contacting: (a) a gaseous mixture comprising: (i) lactic acid, (ii) water, and (iii) nitrogen, wherein said lactic acid is present in an amount of about 2.5 mol % and wherein said water is present in an amount of about 50 mol % based on the total moles of said gaseous mixture, with (b) a catalyst prepared by a method comprising combining $BaHPO_4$ and $KH_2PO_4$ in a molar ratio between about 4:1 and about 1:4 to form a solid mixture, and grinding said solid mixture to produce said catalyst, and wherein, said contacting of said gaseous mixture with said catalyst is performed at a temperature of about 300° C. to about 450° C., at a GHSV of between about 7,200 $h^{-1}$ to about 3,600 $h^{-1}$ and at a pressure of about 360 psig (24.8 barg), in a reactor having an interior surface comprising material selected from the group consisting of quartz and borosilicate glass, whereby acrylic acid is produced as a result of said lactic acid being contacted with said catalyst.

A method for dehydrating glycerin to acrolein is provided. The method includes contacting a glycerin containing stream with a catalyst comprising: (a) the phosphate anions described by formulae (Ia) and (IIa):

$$[H_{(1-\beta)}P_{(1+\beta)}O_{(4+3\beta)}]^{2(1+\beta)-} \quad \text{(Ia)}$$

and

$$[H_{(2-2\gamma)}PO_{4-\gamma}]^{-} \quad \text{(IIa)},$$

and (b) at least two different cations, wherein the catalyst is neutrally charged; wherein β and γ are greater or equal to 0 and less or equal to 1; and wherein the molar ratio of said phosphate anions in the catalyst is between about 0.1 and about 10, whereby acrolein is produced as a result of said glycerin being contacted with the catalyst. Acrolein is an intermediate which can be converted to acrylic acid using conditions similar to what are used today in the second oxidation step in the propylene to acrylic acid process.

A method for dehydrating 3-hydroxypropionic acid, 3-hydroxypropionic acid derivatives, or mixtures thereof to acrylic acid, acrylic acid derivatives, or mixtures thereof is provided. The method includes contacting a 3-hydroxypropionic acid, 3-hydroxypropionic acid derivatives, or mixtures thereof containing stream with a catalyst comprising: (a) the phosphate anions described by formulae (Ia) and (IIa):

$$[H_{(1-\beta)}P_{(1+\beta)}O_{(4+3\beta)}]^{2(1+\beta)-} \quad \text{(Ia)}$$

and

$$[H_{(2-2\gamma)}PO_{4-\gamma}]^{-} \quad \text{(IIa)},$$

and (b) at least two different cations, wherein the catalyst is neutrally charged; further, wherein β and γ are greater or equal to 0 and less or equal to 1; and further, wherein the molar ratio of said phosphate anions in the catalyst is between about 0.1 and about 10, whereby acrylic acid is produced as a result of said 3-hydroxypropionic acid, 3-hydroxypropionic acid derivatives, or mixtures thereof being contacted with the catalyst.

A method for isomerization of lactic acid, lactic acid derivates, and mixtures thereof into 3-hydroxypropionic acid, 3-hydroxypropionic acid derivatives, or mixtures thereof is provided. The method includes contacting: a) lactic acid, lactic acid derivates, and mixtures thereof; b) water, and c) a catalyst comprising: (i) the phosphate anions described by formulae (Ia) and (IIa):

$$[H_{(1-\beta)}P_{(1+\beta)}O_{(4+3\beta)}]^{2(1+\beta)-} \quad \text{(Ia)}$$

and

$$[H_{(2-2\gamma)}PO_{4-\gamma}]^{-} \quad \text{(IIa)},$$

and (ii) at least two different cations, wherein the catalyst is neutrally charged; wherein β and γ are greater or equal to 0 and less or equal to 1; and wherein the molar ratio of said phosphate anions in the catalyst is between about 0.1 and about 10, whereby 3-hydroxypropionic acid, 3-hydroxypropionic acid derivatives, or mixtures thereof are produced as a result of said lactic acid, lactic acid derivates, and mixtures thereof being contacted with the catalyst. In another embodiment of the present invention, said 3-hydroxypropionic acid, 3-hydroxypropionic acid derivatives, or mixtures thereof is further dehydrated to acrylic acid, acrylic acid derivates, and mixtures thereof using a dehydration catalyst.

A method for reduction of lactic acid, lactic acid derivates, and mixtures thereof into propionic acid, propionic acid derivatives, 1-propanol, 1-propanol derivatives, or mixtures thereof is provided. The method includes contacting: a) lactic acid, lactic acid derivatives, and mixtures thereof; b) hydrogen gas, and c) a catalyst comprising: (i) the phosphate anions described by formulae (Ia) and (IIa):

$$[H_{(1-\beta)}P_{(1+\beta)}O_{(4+3\beta)}]^{2(1+\beta)-} \quad \text{(Ia)}$$

and

$$[H_{(2-2\gamma)}PO_{4-\gamma}]^{-} \quad \text{(IIa)},$$

and (ii) at least two different cations, wherein the catalyst is neutrally charged; wherein β and γ are greater or equal to 0 and less or equal to 1; and wherein the molar ratio of said phosphate anions in the catalyst is between about 0.1 and about 10, whereby propionic acid, propionic acid derivatives, 1-propanol, 1-propanol derivatives, or mixtures thereof are produced as a result of said lactic acid, lactic acid derivates, and mixtures thereof being contacted with the catalyst. In another embodiment of the present invention, said catalyst further comprises one or more transition metals selected from the groups 8 to 11 of the periodic table.

Derivatives of propanoic acid can be metal or ammonium salts of propanoic acid, alkyl esters of propanoic acid, or a mixture thereof. Non-limiting examples of metal salts of propanoic acid are sodium propionate, potassium propionate, and calcium propionate. Non-limiting examples of alkyl esters of propanoic acid are methyl propionate, ethyl propionate, butyl propionate, 2-ethylhexyl propionate, or mixtures thereof. A derivative of 1-propanol can be 1-alkyloxypropanol.

V Process for the Production of Acrylic Acid or its Derivatives from Lactic Acid or Its Derivatives The inventors have unexpectedly found that the process of dehydrating lactic acid, lactic acid derivatives, or mixtures thereof can produce high yield to and selectivity of acrylic acid, acrylic acid derivatives, or mixtures thereof when: 1) the solution of lactic acid, lactic acid derivatives, or mixtures thereof has the lactic acid in monomeric form and is combined with an inert gas; 2) the process includes an evaporating step and a dehydrating step; 3) there is a cooling step, with a short residence time, downstream of the dehydrating step; 4) the dehydrating catalyst is according to the present invention; and 5) operating the dehydrating step under a pressure of about 80 psig (5.5 barg) or more or a water partial pressure of about 10 psi (0.7 bar) or more. Not wishing to be bound by theory, inventors believe that: 1) the monomeric form of the lactic acid in solution in the evaporating step is necessary to prevent excessive coking in the dehydrating step; 2) the split of the evaporating and dehydrating steps is necessary to improve the yield to and selectivity of acrylic acid, acrylic acid derivatives, or mixtures thereof; 3) the short duration cooling step is necessary to maintain the high yield to and selectivity of acrylic acid, acrylic acid derivatives, or mixtures thereof achieved at the exit of the dehydrating step; and 4) the elevated water partial pressure enhances the catalytic activity with the formation of hydrated catalysts with Brønsted acidity from less protonated entities in the catalyst during the dehydrating step. Thus, the inventors have also unexpectedly found that the process of dehydrating lactic acid can be more efficient in the presence of water than under water-free conditions as usually preferred in the art.

A process for converting lactic acid, lactic acid derivatives, or mixtures thereof to acrylic acid, acrylic acid derivatives, or mixtures thereof of the present invention comprises the following steps: a) providing an aqueous solution comprising lactic acid, lactic acid derivatives, or mixtures thereof, wherein the lactic acid is in monomeric form in the aqueous solution; b) combining the aqueous solution with an inert gas to form an aqueous solution/gas blend; c) evaporating the aqueous solution gas/blend to produce a gaseous mixture; and d) dehydrating the gaseous mixture by contacting the mixture with a dehydration catalyst under a pressure of at least about 80 psig (5.5 barg).

A process for converting lactic acid, lactic acid derivatives, or mixtures thereof to acrylic acid, acrylic acid derivatives, or mixtures thereof of the present invention comprises the following steps: a) providing an aqueous solution comprising lactic acid, lactic acid derivatives, or mixtures thereof, wherein the lactic acid is in monomeric form in the aqueous solution; b) combining the aqueous solution with an inert gas to form an aqueous solution/gas blend; c) evaporating the aqueous solution gas/blend to produce a gaseous mixture; and d) dehydrating the gaseous mixture by contacting the mixture with any dehydration catalyst disclosed in Section II ("Catalysts for the Conversion of Lactic Acid or its Derivatives to Acrylic Acid or its Derivatives") of the present invention under a water partial pressure of about 10 psi (0.7 bar) or more.

Derivatives of lactic acid can be metal or ammonium salts of lactic acid, alkyl esters of lactic acid, lactic acid oligomers, cyclic di-esters of lactic acid, lactic acid anhydride, 2-alkoxypropoanoic acids or their alkyl esters, 2-aryloxypropanoic acids or their alkyl esters, 2-acyloxypropanoic acids or their alkyl esters, or a mixture thereof. Non-limiting examples of metal salts of lactic acid are sodium lactate, potassium lactate, and calcium lactate. Non-limiting examples of alkyl esters of lactic acid are methyl lactate, ethyl lactate, butyl lactate, 2-ethylhexyl lactate, or mixtures thereof. A non-limiting example of cyclic di-esters of lactic acid is dilactide. Non-limiting examples of 2-alkoxypropoanoic acids are 2-methoxypropanoic acid and 2-ethoxypropanoic acid. A non-limiting example of 2-aryloxypropanoic acid is 2-phenoxypropanoic acid. A non-limiting example of 2-acyloxypropanoic acid is 2-acetoxypropanoic acid.

Lactic acid can be in monomeric form or as oligomers in an aqueous solution of lactic acid, lactic acid derivatives, or mixtures thereof. In one embodiment of the present invention, the oligomers of the lactic acid in an aqueous solution of lactic acid, lactic acid derivatives, or mixtures thereof are less than about 25 wt % based on the total amount of lactic acid, lactic acid derivatives, or mixtures thereof. In another embodiment of the present invention, the oligomers of the lactic acid in an aqueous solution of lactic acid, lactic acid derivatives, or mixtures thereof are less than about 10 wt % based on the total amount of lactic acid, lactic acid derivatives, or mixtures thereof. In another embodiment of the present invention, the oligomers of the lactic acid in an aqueous solution of lactic acid, lactic acid derivatives, or mixtures thereof are less than about 5 wt % based on the total amount of lactic acid, lactic acid derivatives, or mixtures thereof. In yet another embodiment of the present invention, the lactic acid is in monomeric form in an aqueous solution of lactic acid, lactic acid derivatives, or mixtures thereof. The process steps to remove the oligomers from the aqueous solution can be purification or diluting with water and heating. In one embodiment of the present invention, the heating step can involve heating the aqueous solution of lactic acid, lactic acid derivatives, or mixtures thereof at a temperature between about 50° C. to about 100° C. to remove the oligomers of the lactic acid. In another embodiment of the present invention, the heating step can involve heating the lactic acid aqueous solution at a temperature between about 95° C. to about 100° C. to remove the oligomers of the lactic acid and produce a monomeric lactic acid aqueous solution comprising at least 95 wt % of lactic acid in monomeric form based on the total amount of lactic acid. In another embodiment of the present invention, an about 88 wt % lactic acid aqueous solution (e.g. from Purac Corp., Lincolnshire, Ill.) is diluted with water to form an about 20 wt % lactic acid aqueous solution and remove the ester impurities that are produced from the intermolecular condensation reaction. These esters can result in loss of product due to their high boiling point and oligomerization in the evaporating stage of the process. Additionally, these esters can cause coking, catalyst deactivation, and reactor plugging. As the water content decreases in the aqueous solution, the loss of feed material to the catalytic reaction, due to losses in the evaporating step, increases.

Lactic acid can be L-lactic acid, D-lactic acid, or mixtures thereof. In one embodiment of the present invention, the lactic acid derivative is methyl lactate. Methyl lactate can be neat or in an aqueous solution.

Acrylic acid derivatives can be metal or ammonium salts of acrylic acid, alkyl esters of acrylic acid, acrylic acid oligomers, or a mixture thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

In one embodiment of the present invention, the concentration of the lactic acid, lactic acid derivatives, or mixtures thereof in the aqueous solution is between about 5 wt % and about 50 wt %. In another embodiment of the present invention, the concentration of the lactic acid, lactic acid derivatives, or mixtures thereof in the aqueous solution is between about 10 wt % and about 25 wt %. In yet another embodiment of the present invention, the concentration of the lactic acid, lactic acid derivatives, or mixtures thereof in the aqueous solution is about 20 wt %.

In one embodiment of the present invention, the aqueous solution comprises antioxidant. In another embodiment of the present invention, the aqueous solution comprises butylated hydroxyl toluene (BHT), butylated hydroxyl anisole (BHA), or mixtures thereof. In yet another embodiment of the present invention, the aqueous solution comprises ethylene glycol, ethanedithiol, methanol, methanethiol, or mixtures thereof.

The aqueous solution can be combined with an inert gas to form an aqueous solution/gas blend. Non-limiting examples of the inert gas are air, nitrogen, helium, argon, carbon dioxide, carbon monoxide, steam, and mixtures thereof. The inert gas can be introduced to the evaporating step separately or in combination with the aqueous solution. The aqueous solution can be introduced with a simple tube or through atomization nozzles. Non-limiting examples of atomization nozzles include fan nozzles, pressure swirl atomizers, air blast atomizers, two-fluid atomizers, rotary atomizers, and supercritical carbon dioxide atomizers. In one embodiment of the present invention, the droplets of the aqueous solution are less than about 500 μm in diameter. In another embodiment of the present invention, the droplets of the aqueous solution are less than about 200 μm in diameter. In yet another embodiment of the present invention, the droplets of the aqueous solution are less than about 100 μm in diameter.

In the evaporating step, the aqueous solution/gas blend is heated to give a gaseous mixture. In one embodiment of the present invention, the temperature during the evaporating step is between about 165° C. to about 450° C. In another embodiment of the present invention, the temperature during the evaporating step is between about 250° C. to about 375° C. In another embodiment of the present invention, the temperature during the evaporating step is between about 300° C. to about 375° C. In one embodiment of the present invention, the gas hourly space velocity (GHSV) in the evaporating step is between about 720 $h^{-1}$ to 7,200 $h^{-1}$. In another embodiment of the present invention, the gas hourly space velocity (GHSV) in the evaporating step is between about 6,000 $h^{-1}$ to about 7,200 $h^{-1}$. In another embodiment of the present invention, the gas hourly space velocity (GHSV) in the evaporating step is between about 720 $h^{-1}$ to about 3,600 $h^{-1}$. The evaporating step can be performed at either atmospheric pressure or higher pressure. In one embodiment of the present invention, the evaporating step is performed under a pressure between about 80 psig (5.5 barg) to about 550 psig (37.9 barg). In another embodiment of the present invention, the evaporating step is performed under a pressure between about 300 psig (20.7 barg) to about 400 psig (27.6 barg). In yet another embodiment of the present invention, the evaporating step is performed under a pressure between about 350 psig (24.1 barg) to about 375 psig (25.9 barg). In one embodiment of the present invention, the gaseous mixture comprises between about 0.5 mol % to about 50 mol % lactic acid, lactic acid derivatives, or mixtures thereof. In another embodiment of the present invention, the gaseous mixture comprises between about 1 mol % to about 10 mol % lactic acid, lactic acid derivatives, or mixtures thereof. In another embodiment of the present invention, the gaseous mixture comprises between about 1.5 mol % to about 3.5 mol % lactic acid, lactic acid derivatives, or mixtures thereof. In another embodiment of the present invention, the gaseous mixture comprises about 2.5 mol % lactic acid, lactic acid derivatives, or mixtures thereof.

The evaporating step can be performed in various types of equipment, such as, but not limited to, plate heat exchanger, empty flow reactor, and fixed bed flow reactor. Regardless of the type of the reactor, in one embodiment of the present invention, the reactor has an interior surface comprising material selected from the group consisting of quartz, borosilicate glass, silicon, manufactured sapphire, and mixtures thereof. In another embodiment of the present invention, the reactor has an interior surface comprising material selected from the group consisting of passivated hastelloy, passivated inconel, passivated stainless steel, and mixtures thereof. In one embodiment of the present invention, the reactor has an interior surface comprising material selected from the group consisting of quartz, borosilicate glass, silicon, and mixtures thereof. In another embodiment of the present invention, the reactor has an interior surface comprising material with less than 0.1% of Group 8-11 transition metals. In yet another embodiment of the present invention, the reactor has an interior surface comprising material with less than 0.01% of Group 8-11 transition metals. In one embodiment of the present invention, the reactor has an interior surface comprising a passivated material. Not wishing to be bound by theory, inventors believe that Group 8-11 transition metals may accelerate side reactions leading to formation of acetaldehyde, propanoic acid, 1,2-propanediol, and hydroxyacetone and decreasing the acrylic acid selectivity. The evaporating step can be performed in a reactor with the aqueous solution flowing down, or flowing up, or flowing horizontally. In one embodiment of the present invention, the evaporating step is performed in a reactor with the aqueous solution flowing down. Also, the evaporating step can be done in a batch form.

The gaseous mixture from the evaporating step is converted to acrylic acid, acrylic acid derivatives, and mixture thereof by contact it with a dehydration catalyst in the dehydrating step. The dehydration catalyst can be selected from the group comprising sulfates, phosphates, metal oxides, aluminates, silicates, aluminosilicates (e.g., zeolites), arsenates, nitrates, vanadates, niobates, tantalates, selenates, arsenatophosphates, phosphoaluminates, phosphoborates, phosphocromates, phosphomolybdates, phosphosilicates, phosphosulfates, phosphotungstates, and mixtures thereof, and others that may be apparent to those having ordinary skill in the art. The catalyst can contain an inert support that is constructed of a material comprising silicates, aluminates, carbons, metal oxides, and mixtures thereof. In one embodiment of the present invention, the dehydrating step is performed in a reactor, wherein the reactor has an interior surface comprising material selected from the group consisting of quartz, borosilicate glass, silicon, manufactured sapphire, and mixtures thereof. In another embodiment of the present invention, the reactor has an interior surface comprising material selected from the group consisting of passivated hastelloy, passivated inconel, passivated stainless steel, and mixtures thereof. In another embodiment of the present invention, the dehydrating step is performed in a reactor, wherein the reactor has an interior surface comprising material selected from the group consisting of quartz, borosilicate glass, and mixtures thereof. In one embodiment of the present invention, the reactor has an interior surface comprising material with less than 0.1% of Group 8-11 transition metals. In another embodiment of the present invention, the reactor has an interior surface comprising material with less than 0.01% of Group 8-11 transition metals. In yet another embodiment of the present invention, the reactor has an interior surface comprising a passivated material. In one embodiment of the present invention, the temperature during the dehydrating step is between about 150° C. to about 500° C. In another embodiment of the present invention, the temperature during the dehydrating step is between about 300° C. to about 450° C. In yet another embodiment of the present invention, the temperature during the dehydrating step is between about 350° C. to about 425° C. In one embodiment of the present invention, the GHSV in the dehydrating step is between about 720 $h^{-1}$ to about 36,000 $h^{-1}$. In another embodiment of the present invention, the GHSV in the dehydrating step is about 3,600 $h^{-1}$. The dehydrating step is performed at higher than atmospheric pressure. In one embodiment of the present invention, the dehydrating step is performed under a pressure of at least about 80 psig (5.5 barg). In another embodiment of the present invention, the dehydrating step is performed under a pressure between about 80 psig (5.5 barg) to about 550 psig (37.9 barg). In another embodiment of the present invention, the dehydrating step is performed under a pressure between about 150 psig (10.3 barg) to about 500 psig (34.5 barg). In yet another embodiment of the present invention, the dehydrating step is performed under a pressure between about 300 psig (20.7 barg) to about 400 psig (27.6 barg). In one embodiment of the present invention, the dehydrating step is performed under a pressure of about 360 psig (24.8 barg).

In one embodiment of the present invention, the dehydrating step is performed at a water partial pressure of about 10 psi (0.7 bar) or more. In another embodiment of the present invention, the dehydrating step is performed at a water partial pressure between about 10 psi (0.7 bar) and 500 psi (34.5 bar). In yet another embodiment of the present invention, the dehydrating step is performed at a water partial pressure between about 15 psi (1 bar) and about 320 psi (22.1 bar). In one embodiment of the present invention, the dehydrating step is performed at a water partial pressure of about 186 psi (12.8 bar).

The dehydrating step can be performed in a reactor with the gaseous mixture flowing down, flowing up, or flowing horizontally. In one embodiment of the present invention, the dehydrating step is performed in a reactor with the gaseous mixture flowing down. Also, the dehydrating step can be done in a batch form.

In one embodiment of the present invention, the evaporating and dehydrating steps are combined in a single step. In another embodiment of the present invention, the evaporating and dehydrating steps are performed sequentially in a single reactor. In yet another embodiment of the present invention, the evaporating and dehydrating steps are performed sequentially in a tandem reactor.

In one embodiment of the present invention, the selectivity of acrylic acid, acrylic acid derivatives, and mixture thereof from lactic acid, lactic acid derivatives, or mixtures thereof is at least about 50%. In another embodiment of the present invention, the selectivity of acrylic acid, acrylic acid derivatives, and mixture thereof from lactic acid, lactic acid derivatives, or mixtures thereof is at least about 80%. In one embodiment of the present invention, the selectivity of propanoic acid from lactic acid, lactic acid derivatives, or mixtures thereof is less than about 5%. In another embodiment of the present invention, the selectivity of propanoic acid from lactic acid, lactic acid derivatives, or mixtures thereof is less than about 1%. In one embodiment of the present invention, the conversion of the lactic acid, lactic acid derivatives, or mixtures thereof is more than about 50%. In another embodiment of the present invention, the conversion of the lactic acid, lactic acid derivatives, or mixtures thereof is more than about 80%.

In another embodiment of the present invention, a process for converting lactic acid, lactic acid derivatives, or mixtures thereof to acrylic acid, acrylic acid derivatives, or mixtures thereof is provided. The process comprises the following steps: a) providing an aqueous solution comprising lactic acid, lactic acid derivatives, or mixtures thereof, wherein the lactic acid comprises oligomers in the aqueous solution; b) heating the aqueous solution at a temperature between about 50° C. to about 100° C. to remove the oligomers of the lactic acid and produce an aqueous solution of monomeric lactic acid; c) combining the aqueous solution of monomeric lactic acid with an inert gas to form an aqueous solution/gas blend; d) evaporating the aqueous solution gas/blend to produce a gaseous mixture; and e) dehydrating the gaseous mixture by contacting the mixture with a dehydration catalyst and producing the acrylic acid, acrylic acid derivatives, or mixtures thereof.

In one embodiment of the present invention, after the heating step, the concentration of the oligomers of the lactic acid in the aqueous solution of monomeric of monomeric lactic acid is less than about 20 wt % based on the total amount of lactic acid, lactic acid derivatives, or mixtures thereof. In another embodiment of the present invention, after the heating step, the concentration of the oligomers of the lactic acid in the aqueous solution of monomeric of monomeric lactic acid is less than about 5 wt % based on the total amount of lactic acid, lactic acid derivatives, or mixtures thereof.

In another embodiment of the present invention, a process for converting lactic acid, lactic acid derivatives, or mixtures thereof to acrylic acid, acrylic acid derivatives, and mixture thereof is provided. The process comprises the following steps: a) providing an aqueous solution comprising lactic acid, lactic acid derivatives, or mixtures thereof, wherein the lactic acid is in monomeric form in the aqueous solution; b) combining the aqueous solution with an inert gas to form an aqueous solution/gas blend; c) evaporating the aqueous solution/gas blend to produce a gaseous mixture; d) dehydrating the gaseous mixture by contacting the mixture with a dehydration catalyst, at a water partial pressure of about 10 psi (0.7 bar) or more, producing acrylic acid, and/or acrylates; and e) cooling the acrylic acid, acrylic acid derivatives, and mixture thereof at a GHSV of more than about 360 $h^{-1}$.

The stream of acrylic acid, acrylic acid derivatives, and mixture thereof produced in the dehydrating step is cooled to give an aqueous acrylic acid composition as the product stream. The time required to cool stream of the acrylic acid, acrylic acid derivatives, or mixtures thereof must be controlled to reduce the decomposition of acrylic acid to ethylene and polymerization. In one embodiment of the present invention, the GHSV of the acrylic acid, acrylic acid derivatives, and mixture thereof in the cooling step is between about 360 $h^{-1}$ to about 36,000 $h^{-1}$.

In another embodiment of the present invention, a process for converting lactic acid to acrylic acid is provided. The process comprises the following steps: a) diluting an about 88 wt % lactic acid aqueous solution with water to form an about 20 wt % lactic acid aqueous solution; b) heating the about 20 wt % lactic acid aqueous solution at a temperature of about 95° C. to about 100° C. to remove oligomers of the lactic acid, producing a monomeric lactic acid solution comprising at least about 95 wt % of the lactic acid in monomeric form based on the total amount of lactic acid; c) combining the monomeric lactic acid solution with nitrogen to form an aqueous solution/gas blend; d) evaporating the aqueous solution/gas blend in a reactor with inside surface of borosilicate glass at a GHSV of about 6,000 $h^{-1}$ to about 7,200 $h^{-1}$ at a temperature between about 300° C. to about 375° C. to produce a gaseous mixture comprising about 2.5 mol % lactic acid and about 50 mol % water; e) dehydrating the gaseous mixture in a reactor with inside surface of borosilicate glass at a GHSV of about 3,600 $h^{-1}$ at a temperature of 350° C. to about 425° C. by contacting the mixture with a dehydration catalyst under a pressure of about 360 psig (24.8 barg) producing the acrylic acid; and f) cooling the acrylic acid at a GHSV between about 360 $h^{-1}$ to about 36,000 $h^{-1}$. In yet another embodiment of the present invention, the dehydration catalyst is any catalyst disclosed in Section II ("Catalysts for the Conversion of Lactic Acid or its Derivatives to Acrylic Acid or its Derivatives") of the present invention and the dehydrating step is performed under a water partial pressure of about 10 psi (0.7 bar) or more.

In another embodiment of the present invention, a process for converting lactic acid, derivatives of lactic acid, and mixtures thereof to acrylic acid, acrylic acid derivatives, or mixtures thereof is provided. The process comprises the following steps: a) providing an aqueous solution comprising lactic acid, lactic acid derivatives, or mixtures thereof, wherein the lactic acid is in monomeric form in the aqueous solution, and wherein the lactic acid, lactic acid derivatives, or mixtures thereof comprise between about 10 wt % to about 25 wt % of the aqueous solution; b) combining the aqueous solution with an inert gas to form an aqueous solution/gas blend; c) evaporating the aqueous solution/gas blend to produce a gaseous mixture; and d) dehydrating the gaseous mixture by contacting the mixture with a dehydration catalyst producing acrylic acid, acrylic acid derivatives, or mixtures thereof.

In another embodiment of the present invention, a process for converting alkyl lactates to acrylic acid, acrylic acid derivatives, or mixtures thereof is provided. The process comprises the following steps: a) providing alkyl lactates or a solution comprising alkyl lactates and a solvent; b) combining the alkyl lactates or the solution comprising the alkyl lactates and the solvent with an inert gas to form a liquid gas blend; c) evaporating the liquid gas blend to produce a gaseous mixture; and d) dehydrating the gaseous mixture by contacting the gaseous mixture with a dehydration catalyst under a pressure of at least about 80 psig (5.5 barg), producing acrylic acid, acrylic acid derivatives, or mixtures thereof.

In one embodiment of the present invention, alkyl lactates are selected from the group consisting of methyl lactate, ethyl lactate, butyl lactate, 2-ethylhexyl lactate, and mixtures thereof. In another embodiment of the present invention, the solvent is selected from the group consisting of water, methanol, ethanol, butanol, 2-ethylhexanol, isobutanol, isooctyl alcohol, and mixtures thereof.

In another embodiment of the present invention, a process for converting lactic acid, lactic acid derivatives, or mixtures thereof to acrylic acid, acrylic acid derivatives, or mixtures thereof is provided comprising the following steps: a) providing a solution comprising lactic acid, lactic acid derivatives, or mixtures thereof; b) combining the solution with a gas to form a solution/gas blend; and c) dehydrating the solution/gas blend by contacting the solution/gas blend with a dehydration catalyst.

In another embodiment of the present invention, the dehydration occurs in the liquid phase, at least partially. In yet another embodiment of the present invention, the dehydration occurs in the aqueous phase, at least partially. In one embodiment of the present invention, the liquid phase dehydration is carried out in an apparatus, which is pressurized to ensure that all major components are in the liquid phase. In another embodiment of the present invention, the liquid phase dehydration is carried out in an apparatus, which is operated at low temperature to ensure that all major components are in the liquid phase. In yet another embodiment of the present invention, the liquid phase comprises a solvent. Non-limiting examples of solvents are hydrocarbons, chlorinated hydrocarbons, fluorinated hydrocarbons, brominated hydrocarbons, esters, ethers, ketones, aldehydes, acids, alcohols, or mixtures thereof. The liquid-phase dehydration can be conducted by using various methods, known to those skilled in the art, such as, by way of example and not limitation, fixed bed reactor, single-stage stirred tank reactor, multi-stage stirred tank reactor, multi-stage distillation column, and combinations thereof. These methods may be conducted batch-wise or continuously.

In one embodiment of the present invention, the dehydration or isomerizations reactions of lactic acid derivatives or mixtures thereof occur in the aqueous phase, at least partially, and the pH of the reaction is between about 3 and about 8. In another embodiment of the present invention, the pH of the reaction in the aqueous phase is between about 4 and about 7. In yet another embodiment of the present invention, the pH of the reaction in the aqueous phase is between about 5 and about 6.

In one embodiment of the present invention, the dehydration occurs in the liquid phase using any catalyst disclosed in Section II ("Catalysts for the Conversion of Lactic Acid or its Derivatives to Acrylic Acid or its Derivatives") of the present invention.

VI EXAMPLES

The following examples are provided to illustrate the invention, but are not intended to limit the scope thereof.

Example 1

Potassium phosphate dibasic, $K_2HPO_4$ (4.37 g, 25.1 mmol; Sigma-Aldrich Co., St. Louis, Mo.; catalog #60347); barium nitrate, $Ba(NO_3)_2$ (19.60 g, 75.0 mmol; Sigma-Aldrich Co., St. Louis, Mo.; catalog #202754); and crystalline phosphoric acid, $H_3PO_4$ (9.81 g, 100.1 mmol; Sigma-Aldrich Co., St. Louis, Mo.; catalog #466123) were ground and mixed together using a mortar and pestle to provide a paste containing potassium ($K^+$, $M^I$) and barium ($Ba^{2+}$, $M^{II}$), cations. The material was calcined in a oven with air circulation (G1530A, HP6890 GC; Agilent Corp., Santa Clara, Calif.) at 450° C. for 4 hours (1° C./min ramp). After calcination, the material was left inside the oven until it cooled down at a temperature of 25° C. before it was taken out of the oven. Finally, the catalyst was ground and sieved to about 106 μm to about 212 μm.

Example 2

454 g of an 88 wt % L-lactic acid solution (Purac Corp., Lincolnshire, Ill.) was diluted with 1,300 g of water. The diluted solution was heated to 95° C. and held at that temperature with stirring for about 4 to 12 hours. Then, the solution was cooled to room temperature, and its lactic acid and lactic acid oligomers concentrations were measured by HPLC (Agilent 1100 system; Santa Clara, Calif.) equipped with a DAD detector and a Waters Atlantis T3 column (Catalog #186003748; Milford, Mass.) using methods generally known by those having ordinary skill in the art. The solution was essentially free of oligomers. Finally, the solution was further diluted with water to yield a 20 wt % L-lactic acid aqueous solution and essentially free of oligomers.

Example 3

A 13 inch (330 mm) long stainless steel glass-lined tube (SGE Analytical Science Pty Ltd., Ringwood, Australia) with a 4.0 mm internal diameter (ID) was packed with glass wool (2 Inch/51 mm bed length), topped by catalyst prepared as described in Example 1 (1.6 cm³ bed volume, 5 inch/127 mm bed length) and 0.96 cm³ (3 inch; 76.2 mm) of free space at the top of the reactor in the heated zone. The tube was placed inside an aluminum block and placed in a clam shell furnace series 3210 (Applied Test Systems, Butler, Pa.) such as the bottom of the packed bed was aligned with the bottom of the aluminum block. The reactor was set-up in a down-flow arrangement and was equipped with a Knauer Smartline 100 feed pump (Berlin, Germany), a Brooks 0254 gas flow controller (Hatfield, Pa.), a Brooks back pressure regulator, and a Teflon-lined catch tank. The head of the reactor was fitted with a ⅛" (3.2 mm) stainless steel nitrogen feed line and a 1/16" (1.6 mm) fused silica lined stainless steel liquid feed supply line connected to the feed pump. The bottom of the reactor was connected to the catch tank using 1/8" (3.2 mm) fused silica lined stainless steel tubing and Swagelok™ fittings. The clam shell furnace was heated such that the reactor wall temperature was kept constant at about 375° C. during the course of the reaction. The reactor was supplied with separate liquid and gas feeds that were mixed together before reaching the catalyst bed. The gas feed was composed of molecular nitrogen ($N_2$) at 360 psig (24.8 barg) and at a flow of 45 mL/min. The liquid feed was an aqueous solution of lactic acid (20 wt % L-lactic acid) and was fed at 0.045 mL/min. The GHSV in the evaporating zone was about 5,900 $h^{-1}$, and the GHSV in the dehydrating zone was about 3,500 $h^{-1}$. The LHSV in the dehydrating zone was about 1.8 $h^{-1}$. The gas phase concentrations were: nitrogen: 47.9 mol %; lactic acid: 2.5 mol %; and water: 49.6 mol %. The water partial pressure was 186 psi (12.8 bar). The gaseous mixture was cooled and the liquid stream was collected in the catch tank for analysis by off-line HPLC using an Agilent 1100 system (Santa Clara, Calif.) equipped with a diode array detector (DAD) and a Waters Atlantis T3 column (Catalog #186003748; Milford, Mass.) and by off-line GC using a Hewlett Packard HP6890 series system (Santa Clara, Calif.) equipped with a FID detector and Agilent CP-Wax 58 FFAP CB column (Catalog # CP7717; Santa Clara, Calif.), using methods generally known by those having ordinary skill in the art. The gaseous mixture was analyzed on-line by GC using an Agilent 7890 system (Santa Clara, Calif.) equipped with a FID detector and Varian CP-Para Bond Q column (Catalog # CP7351; Santa Clara, Calif.). The crude reaction mixture was cooled and collected at various time points over a period of 144 h. The average acrylic acid yield was 88±2 mol %, average lactic acid conversion was 98±2 mol %, and average acrylic acid selectivity was 90±1 mol %. The total carbon balance was 99.3±1.4%. The average aqueous concentrations of chemicals in the output liquid stream, over the same period of time, were: acrylic acid: 14.7 wt %, acetaldehyde: 0.43 wt %, lactic acid: 0.4 wt %, 2,3-pentanedione: 0.09 wt %, acetic acid: 0.06 wt %, propionic acid: 0.05 wt %, acrylic acid dimer: 0.04%, and hydroxyacetone: 0.03 wt %.

Example 4

Barium nitrate ($Ba(NO_3)_2$; 99.7 wt %; 100.00 g; 381.5 mmol), dipotassium phosphate ($K_2HPO_4$; 100 wt %; 22.23 g; 127.7 mmol), and ammonium phosphate dibasic (($NH_4)_2HPO_4$; 99.2 wt %; 67.24 g; 509.1 mmol), were combined and ground together using a planetary ball mill (PM 100; Retsch (Haan, Germany), catalog #20.540.0003; grinding jar: Zirconium oxide, V=250 mL; Retsch (Haan, Germany), catalog #01.462.0219; grinding balls: Zirconium oxide, D=20 mm; Retsch (Haan, Germany), catalog #05.368.0093; 15 grinding balls, 500 rpm, 15 min, 1 min reverse rotation intervals) to obtain a fine solid mixture. Then, the mixture was transferred to a 1 L glass beaker and calcined using a furnace with air circulation (Nabertherm furnace N30/85 HA with P300 controller, automatic control for exhaust system, and over-temperature limit controller; Nabertherm (Lilienthal, Germany), catalog # N30/85 HA; 450° C., 12 h, 2° C./min heating ramp, open exhaust). After calcination, the material was kept inside the oven until it reached a temperature below 100° C. (no cooling ramp).

The calcined solid was ground gently using a ceramic mortar and pestle to obtain particles of less than about 1 cm and manually separated using sieves No. 70 and No. 140 (USA standard testing sieves, ASTM E-11 specifications; Gilson Company (Lewis Center, Ohio); sieve No. 70 (212 μm, 0.0083"), Ser. No. 11/327,072, and sieve No. 140 (106 μm, 0.0042"), Ser. No. 11/476,914). Particles retained on sieve No. 70 were ground using the ball mill (5 grinding balls, 300 rpm, 30 s, no intervals), followed by sieving using a sieve shaker (Vibratory sieve shaker AS 200 control; Retsch (Haan, Germany), catalog #30.018.0001; 5 min, 1.30 mm amplitude, sieves No. 70 and 140). The process of grinding particles retained on sieve No. 70 followed by sieving was repeated three more times under the same conditions until all the material passed sieve No. 70. Finally, the solid retained on sieve No. 140 was re-sieved (30 min, 1.30 mm amplitude, sieve No. 140) to completely remove small particles and obtain a catalyst with particle size between 106 μm and 212 μm.

Example 5

A 14" (356 mm) long stainless steel glass-lined tube (SGE Analytical Science Pty Ltd., Ringwood, Australia) with a 4.0 mm internal diameter (ID) was packed with 2" (51 mm) of glass wool at the bottom. Then, a homogeneous mixture of: 1) 0.85 g of fused silicon dioxide (Sigma-Aldrich catalog #: 342831; 4-20 mesh) ground and sieved to 106-212 μm, and 2) 0.85 g of catalyst prepared as described in Example 4 was packed on top of the glass wool section to give 1.6 $cm^3$ catalyst bed volume (5"; 127 mm bed length). Finally, 0.96 $cm^3$ (3"; 76.2 mm bed length) of free space was left at the top of the catalyst bed in the heated zone to serve as the evaporator.

The tube was placed inside an aluminum block and placed in a clam shell furnace series 3210 (Applied Test Systems, Butler, Pa.), such as the bottom of the packed bed was aligned with the bottom of the aluminum block. The reactor was set-up in a down-flow arrangement and was equipped with a Knauer Smartline 100 feed pump (Berlin, Germany), a Brooks 0254 gas flow controller (Hatfield, Pa.), a Brooks back pressure regulator, and a Teflon-lined catch tank. The head of the reactor was fitted with a 1/8" (3.2 mm) stainless steel nitrogen feed line and a 1/16" (1.6 mm) polyetheretherketone (PEEK™) tubing (Upchurch Scientific®) liquid feed supply line connected to the feed pump. The bottom of the reactor was connected to the catch tank using 1/8" (3.2 mm) fused silica lined stainless steel tubing and Swagelok™ fittings. The clam shell furnace was heated such that the reactor wall temperature was kept constant at about 375° C. during the course of the reaction.

The reactor was supplied with separate liquid and gas feeds that were mixed together before reaching the catalyst bed. The gas feed was composed of molecular nitrogen ($N_2$) at 360 psig (24.8 barg) and at a flow of 45 mL/min. The liquid feed was an aqueous solution of lactic acid (20 wt % L-lactic acid; see Example 2) and was fed at 0.045 mL/min. The GHSV in the evaporating zone was about 5,900 $h^{-1}$, and the GHSV in the dehydrating zone was about 3,500 $h^{-1}$. The LHSV in the dehydrating zone was about 1.8 $h^{-1}$. The gas phase concentrations were: nitrogen: 47.9 mol %; lactic acid: 2.5 mol %; and water: 49.6 mol %. The water partial pressure was 186 psi (12.8 bar). The gaseous mixture was cooled and the liquid stream was collected in the catch tank for analysis by off-line HPLC using an Agilent 1100 system (Santa Clara, Calif.) equipped with a diode array detector (DAD) and a Waters Atlantis T3 column (Catalog #186003748; Milford, Mass.) and by off-line GC using a Hewlett Packard HP6890 series system (Santa Clara, Calif.) equipped with a FID detector and Agilent CP-Wax 58 FFAP CB column (Catalog # CP7717; Santa Clara, Calif.), using methods generally known by those having ordinary skill in the art. The gaseous mixture was analyzed on-line by GC using an Agilent 7890 system (Santa Clara, Calif.) equipped with a FID detector and Varian CP-Para Bond Q column (Catalog # CP7351; Santa Clara, Calif.).

The crude reaction mixture was cooled and collected at various time points over a period of 31.8 h. The acrylic acid yield was 74.0 mol %, lactic acid conversion was 90.5 mol %, acrylic acid selectivity was 81.8 mol %, and propanoic acid selectivity was 2.7 mol %.

Example 6

A 14" (356 mm) long stainless steel glass-lined tube (SGE Analytical Science Pty Ltd., Ringwood, Australia) with a 4.0 mm internal diameter (ID) was packed with 2" (51 mm) of glass wool at the bottom. Then, a homogeneous mixture of: 1) 0.85 g of fused silicon dioxide (Sigma-Aldrich catalog #: 342831; 4-20 mesh) ground and sieved to 106-212 µm, and 2) 0.85 g of catalyst prepared as described in Example 4 was packed on top of the glass wool section to give 1.6 cm$^3$ catalyst bed volume (5"; 127 mm bed length). Finally, 1.0 g of fused silicon dioxide, ground and sieved to 500-600 µm (Sigma-Aldrich catalog #: 342831; 4-20 mesh), was packed on top of the catalyst bed to give an evaporator with 0.96 cm$^3$ volume (3"; 76.2 mm bed length) in the heated zone.

The tube was placed inside an aluminum block and placed in a clam shell furnace series 3210 (Applied Test Systems, Butler, Pa.), such as the bottom of the packed bed was aligned with the bottom of the aluminum block. The reactor was set-up in a down-flow arrangement and was equipped with a Knauer Smartline 100 feed pump (Berlin, Germany), a Brooks 0254 gas flow controller (Hatfield, Pa.), a Brooks back pressure regulator, and a Teflon-lined catch tank. The head of the reactor was fitted with a ⅛" (3.2 mm) stainless steel nitrogen feed line and a 1/16" (1.6 mm) polyetheretherketone (PEEK™) tubing (Upchurch Scientific®) liquid feed supply line connected to the feed pump. The bottom of the reactor was connected to the catch tank using ⅛" (3.2 mm) fused silica lined stainless steel tubing and Swagelok™ fittings. The clam shell furnace was heated such that the reactor wall temperature was kept constant at about 375° C. during the course of the reaction.

The reactor was supplied with separate liquid and gas feeds that were mixed together before reaching the catalyst bed. The gas feed was composed of molecular nitrogen ($N_2$) at 360 psig (24.8 barg) and at a flow of 45 mL/min. The liquid feed was an aqueous solution of lactic acid (20 wt % L-lactic acid; see Example 2) and was fed at 0.045 mL/min. The GHSV in the evaporating zone was about 5,900 h$^{-1}$, and the GHSV in the dehydrating zone was about 3,500 h$^{-1}$. The LHSV in the dehydrating zone was about 1.8 h$^{-1}$. The gas phase concentrations were: nitrogen: 47.9 mol %; lactic acid: 2.5 mol %; and water: 49.6 mol %. The water partial pressure was 186 psi (12.8 bar). The gaseous mixture was cooled and the liquid stream was collected in the catch tank for analysis by off-line HPLC using an Agilent 1100 system (Santa Clara, Calif.) equipped with a diode array detector (DAD) and a Waters Atlantis T3 column (Catalog #186003748; Milford, Mass.) and by off-line GC using a Hewlett Packard HP6890 series system (Santa Clara, Calif.) equipped with a FID detector and Agilent CP-Wax 58 FFAP CB column (Catalog # CP7717; Santa Clara, Calif.), using methods generally known by those having ordinary skill in the art. The gaseous mixture was analyzed on-line by GC using an Agilent 7890 system (Santa Clara, Calif.) equipped with a FID detector and Varian CP-Para Bond Q column (Catalog # CP7351; Santa Clara, Calif.).

The crude reaction mixture was cooled and collected at various time points over a period of 29.2 h. The acrylic acid yield was 77.7 mol %, lactic acid conversion was 90.7 mol %, acrylic acid selectivity was 85.7 mol %, and propanoic acid selectivity was 1.0 mol %.

Example 7

A 14" (330 mm) long stainless steel glass-lined tube (SGE Analytical Science Pty Ltd., Ringwood, Australia) with a 4.0 mm internal diameter (ID) was packed with 2" (51 mm) of glass wool at the bottom. Then, a homogeneous mixture of: 1) 1.35 g of fused silicon dioxide (Sigma-Aldrich catalog #: 342831; 4-20 mesh) ground and sieved to 106-212 µm, and 2) 1.36 g of catalyst prepared as described in Example 4 was packed on top of the glass wool section to give 2.52 cm$^3$ catalyst bed volume (8"; 203 mm bed length). This setup did not have an evaporator.

The tube was placed inside an aluminum block and placed in a clam shell furnace series 3210 (Applied Test Systems, Butler, Pa.) such as the bottom of the packed bed was aligned with the bottom of the aluminum block. The reactor was set-up in a down-flow arrangement and was equipped with a Knauer Smartline 100 feed pump (Berlin, Germany), a Brooks 0254 gas flow controller (Hatfield, Pa.), a Brooks back pressure regulator, and a Teflon-lined catch tank. The head of the reactor was fitted with a ⅛" (3.2 mm) stainless steel nitrogen feed line and a 1/16" (1.6 mm) polyetheretherketone (PEEK™) tubing (Upchurch Scientific®) liquid feed supply line connected to the feed pump. The bottom of the reactor was connected to the catch tank using ⅛" (3.2 mm) fused silica lined stainless steel tubing and Swagelok™ fittings. The clam shell furnace was heated such that the reactor wall temperature was kept constant at about 375° C. during the course of the reaction.

The reactor was supplied with separate liquid and gas feeds that were mixed together before reaching the catalyst bed. The gas feed was composed of molecular nitrogen ($N_2$) at 360 psig (24.8 barg) and at a flow of 72 mL/min. The liquid feed was an aqueous solution of lactic acid (20 wt % L-lactic acid; see Example 2) and was fed at 0.072 mL/min. The GHSV in the dehydrating zone was about 3,500 h$^{-1}$. The LHSV in the dehydrating zone was about 1.8 h$^{-1}$. The gas phase concentrations were: nitrogen: 47.9 mol %; lactic acid: 2.5 mol %; and water: 49.6 mol %. The water partial pressure was 186 psi (12.8 bar). The gaseous mixture was cooled and the liquid stream was collected in the catch tank for analysis by off-line HPLC using an Agilent 1100 system (Santa Clara, Calif.) equipped with a diode array detector (DAD) and a Waters Atlantis T3 column (Catalog #186003748; Milford, Mass.) and by off-line GC using a Hewlett Packard HP6890 series system (Santa Clara, Calif.) equipped with a FID detector and Agilent CP-Wax 58 FFAP CB column (Catalog # CP7717; Santa Clara, Calif.), using methods generally known by those having ordinary skill in the art. The gaseous mixture was analyzed on-line by GC using an Agilent 7890 system (Santa Clara, Calif.) equipped with a FID detector and Varian CP-Para Bond Q column (Catalog # CP7351; Santa Clara, Calif.).

The crude reaction mixture was cooled and collected at various time points over a period of 30.3 h. The acrylic acid yield was 81.5 mol %, lactic acid conversion was 89.5 mol %, acrylic acid selectivity was 91.1 mol %, and propanoic acid selectivity was 0.1 mol %.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making acrylic acid, acrylic acid derivatives, or mixtures thereof comprising contacting a stream comprising lactic acid, lactic acid derivatives, or mixtures thereof with a catalyst comprising:
   the phosphate anions described by formulae (Ic) and (IIc):

 (Ic),

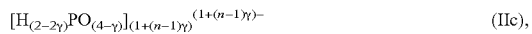 (IIc), and
   at least two different cations,
   wherein the catalyst is neutrally charged, wherein β and γ are greater or equal to 0 and less or equal to 1, wherein n is at least 2, wherein the molar ratio of said phosphate anions in said catalyst is between about 0.1 and about 10, wherein said at least two different cations comprise at least one monovalent cation and at least one polyvalent cation, and wherein said polyvalent cation is selected from the group consisting of the cations of the metals Be, Mg, Ca, Sr, Ba, Sc, Y, Ti, Zr, V, Nb, Cr, Mo, Mn, Ga, Si, Ge, B, Al, In, Tl, Sb, Sn, Bi, Pb, La, Ce, Er, Ac, Th, and mixtures thereof, wherein said stream further comprises:
   a. diluent consisting of water; and
   b. inert gas selected from the group consisting of nitrogen, helium, argon, carbon dioxide, carbon monoxide, and mixtures thereof;
   and further, wherein the water partial pressure in said stream is about 50 psi (3.5 bar) or more.

2. The method of claim 1, wherein the water partial pressure in said stream is between about 10 psi (0.7 bar) and about 500 psi (34.5 bar).

3. The method of claim 1, wherein the water partial pressure in said stream is about 186 psi (12.8 bar).

4. A process for converting lactic acid, lactic acid derivatives, or mixtures thereof to acrylic acid, acrylic acid derivatives, or mixtures thereof comprising the following steps:
   a. providing an aqueous solution comprising lactic acid, lactic acid derivatives, or mixtures thereof, wherein said lactic acid is in monomeric form in said aqueous solution;
   b. combining said aqueous solution with an inert gas to form an aqueous solution/gas blend;
   c. evaporating said aqueous solution/gas blend to produce a gaseous mixture; and
   d. dehydrating said gaseous mixture by contacting said gaseous mixture with a dehydration catalyst under a water partial pressure of about 10 psi (0.7 bar) or more, producing said acrylic acid, acrylic acid derivatives, or mixtures thereof.

5. The process of claim 4, wherein said evaporating step is performed in a reactor, wherein said reactor has a material surface comprising materials with less than 0.1 wt % of Group 8-11 transition metals.

6. The process of claim 4, wherein said dehydrating step is performed in a reactor, wherein said reactor has a material surface comprising materials with less than 0.1 wt % of Group 8-11 transition metals.

7. A process for converting lactic acid to acrylic acid comprising the following steps:
   a. diluting an about 88% lactic acid aqueous solution with water to form an about 20 wt % lactic acid aqueous solution;
   b. heating said about 20 wt % lactic acid aqueous solution at a temperature between about 95° C. to about 100° C. to remove oligomers of said lactic acid, producing a monomeric lactic acid aqueous solution comprising at least 95 wt % of said lactic acid in monomeric form based on the total amount of lactic acid;
   c. combining said monomeric lactic acid aqueous solution with nitrogen to form an aqueous solution/gas blend;
   d. evaporating said aqueous solution/gas blend in a reactor with inside surface of borosilicate glass at a GHSV of about 6,000 h$^{-1}$ to about 7,200 h$^{-1}$ at a temperature between about 300° C. to about 375° C. to produce a gaseous mixture comprising about 2.5 mol % lactic acid and about 50 mol % water;
   e. dehydrating said gaseous mixture in a reactor with inside surface of borosilicate glass at a GHSV of about 3,600 h$^{-1}$ at a temperature between about 350° C. to about 425° C. by contacting said mixture with a dehydration catalyst under a pressure of about 360 psig (24.8 barg), producing said acrylic acid; and
   f. cooling said acrylic acid to give an acrylic acid solution at a GHSV between about 360 h$^{-1}$ to about 36,000 h$^{-1}$.

8. The process of claim 7, wherein said dehydration catalyst is a catalyst comprising:
   the phosphate anions described by formulae (Ic) and (IIc):

 (Ic),

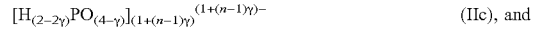 (IIc), and at least two different cations,
   wherein the catalyst is neutrally charged, wherein β and γ are greater or equal to 0 and less or equal to 1, wherein n is at least 2, wherein the molar ratio of said phosphate anions in said catalyst is between about 0.1 and about 10, wherein said at least two different cations comprise at least one monovalent cation and at least one polyvalent cation, and wherein said polyvalent cation is selected from the group consisting of the cations of the metals Be, Mg, Ca, Sr, Ba, Sc, Y, Ti, Zr, V, Nb, Cr, Mo, Mn, Ga, Si, Ge, B, Al, In, Tl, Sb, Sn, Bi, Pb, La, Ce, Er, Ac, Th, and mixtures thereof.

9. A process for converting lactic acid, lactic acid derivatives, or mixtures thereof to acrylic acid, acrylic acid derivatives, or mixtures thereof comprising the following steps:
   a. providing a solution comprising lactic acid, lactic acid derivatives, or mixtures thereof;
   b. combining said solution with a gas to form a solution/gas blend; and
   c. dehydrating said solution/gas blend by contacting said solution/gas blend with a dehydration catalyst;
   said dehydration catalyst comprising:
      i. the phosphate anions described by formulae (Ic) and (IIc):

$$[H_{(1-\beta)}P_{(1+\beta)}O_{(4+3\beta)}]^{2(1+\beta)-} \quad (Ic),$$

$$[H_{(2-2\gamma)}PO_{(4-\gamma)}]_{(1+(n-1)\gamma)}^{(1+(n-1)\gamma)-} \quad (IIc), \text{ and}$$

ii. at least two different cations,
   wherein the catalyst is neutrally charged, wherein β and γ are greater or equal to 0 and less or equal to 1, wherein n is at least 2, wherein the molar ratio of said phosphate anions in said catalyst is between about 0.1 and about 10, wherein said at least two different cations comprise at least one monovalent cation and at least one polyvalent cation, and wherein said polyvalent cation is selected from the group consisting of the cations of the metals Be, Mg, Ca, Sr, Ba, Sc, Y, Ti, Zr, V, Nb, Cr, Mo, Mn, Ga, Si, Ge, B, Al, In, Tl, Sb, Sn, Bi, Pb, La, Ce, Er, Ac, Th, and mixtures thereof.

10. The process of claim 9, wherein said dehydration catalyst comprises:
   a. at least one condensed phosphate anion selected from the group consisting of formulae (I), (II), and (III), $$[P_nO_{3n+1}]^{(n+2)-} \quad (I),$$

$$[P_nO_{3n}]^{n-} \quad (II),$$

$$[P_{(2m+n)}O_{(5m+3n)}]^{n-} \quad (III),$$

wherein n is at least 2 and m is at least 1, and
   b. at least two different cations,
   wherein said catalyst is essentially neutrally charged, and further wherein the molar ratio of phosphorus to the at least two different cations is between about 0.7 and about 1.7.

11. The process of claim 10, wherein said molar ratio of phosphorus to the at least two different cations is about 1.

12. The process of claim 9, wherein said dehydration catalyst comprises:
   monophosphate salts described by the formulae (Ib) and (IIb):

$$M^{II}HPO_4 \quad (Ib)$$

and $$M^{I}H_2PO_4 \quad (IIb),$$

wherein $M^I$ is one or more monovalent cation(s) and $M^{II}$ is one or more divalent cations, and further, wherein the molar ratio of $M^{II}HPO_4$ to $M^{I}H_2PO_4$ is between about 0.1 and about 10.

13. The process of claim 12, wherein said molar ratio of $M^{II}HPO_4$ to $M^{I}H_2PO_4$ in said catalyst is between about 0.2 and about 5.

14. The process of claim 13, wherein said molar ratio of $M^{II}HPO_4$ to $M^{I}H_2PO_4$ in said catalyst is about 1.

* * * * *